(12) United States Patent
Laakkonen et al.

(10) Patent No.: US 7,671,021 B2
(45) Date of Patent: *Mar. 2, 2010

(54) PEPTIDES THAT HOME TO TUMOR LYMPHATIC VASCULATURE AND METHODS OF USING SAME

(75) Inventors: Pirjo Laakkonen, Helsinki (FI); Kimmo Porkka, Helsinki (FI); Jason A. Hoffman, La Jolla, CA (US); Erkki Ruoslahti, Rancho Santa Fe, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 39 days.

This patent is subject to a terminal disclaimer.

(21) Appl. No.: 11/712,043

(22) Filed: Feb. 27, 2007

(65) Prior Publication Data

US 2007/0149444 A1    Jun. 28, 2007

Related U.S. Application Data

(63) Continuation of application No. 10/290,385, filed on Nov. 5, 2002, now Pat. No. 7,192,921.

(60) Provisional application No. 60/421,145, filed on Nov. 8, 2001.

(51) Int. Cl.
    *A61K 38/00*    (2006.01)
(52) U.S. Cl. .................................................. 514/12
(58) Field of Classification Search ............... 514/12
    See application file for complete search history.

(56) References Cited

U.S. PATENT DOCUMENTS

| 5,622,699 A | 4/1997 | Ruoslahti et al. |
| 5,789,542 A | 8/1998 | McLaughlin et al. |
| 7,192,921 B2 * | 3/2007 | Laakkonen et al. ............ 514/12 |

FOREIGN PATENT DOCUMENTS

| EP | 0 927 045 | 12/2005 |
| WO | WO 97/10507 | 3/1997 |
| WO | WO 99/13329 | 3/1999 |
| WO | WO 00/42973 | 7/2000 |
| WO | WO 00/00824 | 1/2002 |

OTHER PUBLICATIONS

Rouslahti (Biochemical Society Transactions 2004; 32: 397-402).*
Laakkonen et al. Nature Medicine 2002; 8: 751-755.*
Arap et al. (Science 1998; 279: 377-380).*
Alvarez-Bravo et al., "Novel synthetic antimicrobial peptides effective against methicillin-resistant *Staphylococcus aureus*," *Biochem. J.* 302:535-538 (1994).
Aoki et al., "Potential tumor-targeting peptide vector of histidylated oligolysine conjugated to a tumor-homing RGD motif," *Cancer Gene. Ther.* 8:783-787 (2001).
Arap et al., "Cancer treatment by targeted drug delivery to tumor vasculature in a mouse model," *Science* 279:377-380 (1998).

Bessalle et al., "All-D-magainin: Chirality, antimicrobial activity and proteolytic resistance," *FEBS Lett* 274:151-155 (1990).
Blondelle and Houghten, "Design of Model Amphipathic Peptides Having Potent Antimicrobial Activities," *Biochemistry* 31:12688-12694 (1992).
Borgstrom et al., "Importance of VEGF for breast cancer angiogenesis in vivo: Implications from intravital microscopy of combination treatments with an anti-VEGF neutralizing monoclonal antibody and doxorubicin," *Anticancer Res.* 19:4203-4214 (1999).
Breiteneder-Geleff et al. "Angiosarcomas express mixed endothelial phenotypes of blood and lymphatic capillaries: Podoplanin as a specific marker for lymphatic endothelium," *American J. of Pathology* 154:385-394 (1999).
Brown et al. "A novel approach for the identification of unique tumor vasculature binding peptides using and *E coli* peptide display library," *Ann. Surg. Oncol.* 7(10):743-749 (2000).
Burg et al. "NG2 proteoglycan-binding peptides target tumor neovasculature," *Cancer Res.*, 59:2869-2874 (1999).
Burgess, et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.* 111(5 Pt 1):2129-2138 (1990).
Chan et al., "Prospective randomized trial of docetaxel versus doxorubicin in patients with metastatic breast cancer," *J. Clin. Oncol.* 17:2341-2354 (1999).
Cortese et al. "Identification of peptides binding to IgG in the CSF of multiple sclerosis patients," *Mult. Scler.* 4 (1):31-36 (1998).
Crown, "The platinum agents: A role in breast cancer treatment," *Seminars in Oncology* 28:28-37 (2001).
Curnis et al., "Enhancement of tumor necrosis factor a antitumor immunotherapeutic properties by targeted delivery to aminopeptidase N (CD13)" *Nat. Bioltechnol.* 18:1185-1190 (2000).
Dekker et al. "Substrate specificity of the integral membrane protease OmpT determined by spatially addressed peptide libraries," *Biochemistry* 40(6):1694-1701 (2001).
Ellerby et al. "Anti-cancer activity of targeted pro-apoptotic peptides," *Nat. Med.* 5(9):1032-1038 (1999).
Ebata et al., "Desmoplakin as a specific marker of lymphatic vessels," *Microvasc. Res.* 61:40-48 (2001).
Fisher et al., "Tamoxifen for prevention of breast cancer: Report of the National Surgical Adjuvant Breast and Bowel Project P-1 Study," *J. Natl. Cancer Instit.* 90:1371-1388 (1998).
Fitzpatrick and Garnett, "Design, synthesis and in vitro testing of methotrexate carrier conjugates linked via oligopeptide spacers," *Anticancer Drug Des.* 10:1-9 (1995).
Fukuda et al., "Anatomic distribution of intraprostatic lymphatics: Implications for the lymphatic spread of prostate cancer—a preliminary study," *Prostate* 44:322-327 (2000).

(Continued)

*Primary Examiner*—Brandon J Fetterolf
(74) *Attorney, Agent, or Firm*—McDermott Will & Emery LLP

(57) ABSTRACT

The present invention provides a conjugate containing a moiety linked to a homing molecule that selectively homes to tumor lymphatic vasculature. The invention also provides a method of directing a moiety to tumor lymphatic vasculature in a subject by administering to the subject a conjugate containing a moiety linked to a homing molecule that selectively homes to tumor lymphatic vasculature.

37 Claims, 14 Drawing Sheets
(6 of 14 Drawing Sheet(s) Filed in Color)

OTHER PUBLICATIONS

Gallouzi and Steitz, "Delineation of mRNA Export Pathways by the Use of Cell-Permeable Peptides," *Science* 294:1895-1901 (2001).
GenBank Accession No. NP_039684.1.
GenBank Accession No. AAB00335.1.
GenBank Accession No. AAG32611.1.
GenBank Accession No. T28529.
GenBank Accession No. NP_073464.
Harris et al., "Cancer of the Breast," In: Cancer: Principles and Practice of Oncology, 4th ed., Chapter 40 (eds. DeVita, Jr., et al.; J.P. Lippincott) (1993).
Karkkainen and Petrova, "Vascular endothelial growth factor receptors in the regulation of angiogenesis and lymphangiogenesis," *Oncogene* 19:5598-5605 (2000).
Laakkonen et al., "A tumor-homing peptide with a targeting specificity related to lymphatic vessels," *Nat. Med.* 8:751-755 (2002).
Lazar, et al., "Transforming growth factor alpha: mutation of aspartic acid 47 and leucine 48 results in different biological activities," *Mol. Cell Bio.* 8: 1247-1252 (1988).
Maloy and Kari, "Structure-activity studies on magainins and other host defense peptides," *Biopolymers* 37:105-122 (1995).
Mancheno et al., "A peptide of nine amino acid residues from α-sarcin cytotoxin is a membrane-perturbing structure," *J. Peptide Res.* 51:142-148 (1998).
Nelson et al. "Murine epidermal growth factor peptide (33-42) binds to a YIGSR-specific laminin receptor on both tumor and endothelial cells," *J. Biol. Chem.*, 271(42):26179-26186 (1996).
Paridaens et al., "Paclitaxel versus doxorubicin as first-line single-agent chemotherapy for metastatic breast cancer: A European Organization for Research and Treatment of Cancer Randomized Study with cross-over," *J. Clin. Oncol.* 18:724-733 (2000).
Pasqualini et al., "α v Integrins as receptors for tumor targeting by circulating ligands," *Nat Biotechnol.* 15(6):542-546 (1997).
Pasqualini et al., "Aminopeptidase N is a receptor for tumor-homing peptides and a target for inhibiting angiogenesis," *Cancer Res.* 60:722-727 (2000).
Pasqualini and Ruoslahti, "Organ targeting in vivo using phage display peptide libraries," *Nature* 380:364-366 (1996).
Prevo et al., "Mouse LYVE-1 is an endocytic receptor for hyaluronan in lymphatic endothelium," *J. Biol. Chem.* 276:19420-19430 (2001).
Rajotte et al., "Molecular heterogeneity of the vascular endothelium revealed by in vivo phage display," *J. Clin. Inv.* 102:430-437 (1998).
Ruoslahti, "Special delivery of drugs by targeting to tissue-specific receptors in the vasculature," *Pharmaceutical News* 7:35-40 (2000).
Rusinko et al., "Using Concord to Construct a Large Database of Three-Dimensional Coordinates from Connection Tables," *J. Chem. Inf. Comput. Sci.* 29:251-255 (1989).
Saberwal and Nagaraj, "Cell-lytic and antibacterial peptides that act by perturbing the barrier function of membranes: Facets of their conformational features, structure-function correlations and membrane-perturbing abilities," *Biochim. Biophys. Acta* 1197:109-131 (1994).
Schneider et al., "Lymphangioblasts in the avian wing bud," *Dev. Dyn.* 216:311-319 (1999).
Schwarze et al., "In Vivo Protein Transduction: Delivery of a Biologically Active Protein into the Mouse," *Science* 285:1569-1572 (1999).
Sidhu et al., "Phage display for selection of novel binding peptides," *Methods Enzym.* 328:333-363 (2000).
Skobe et al., "Induction of tumor lymphangiogenesis by VEGF-C promotes breast cancer metastasis," *Nature Medicine* 7:192-198 (2001).
Stacker et al., "VEGF-D promotes the metastatic spread of tumor cells via the lymphatics," *Nature Medicine* 7:186-191 (2001).
Stewart and Ratain, "Topoisomerase Interactive Agents," Cancer: *Principles and Practice of Oncology*, 5th ed., eds. DeVita, Jr., et al., Chapter 19, pp. 452-467 (1997).
Trepel et al., "Molecular adaptors for vascular-targeted adenoviral gene delivery," *Hum. Gene. Ther.* 11:1971-1981 (2001).
Trzeciak, "Synthesis of head-to-tail cyclized peptides on solid support by Fmoc [9-fluorenylmethoxycarbonyl) chemistry," (abstract) *Tetrahedron Lett*, 1991 Abstract, 612937 (1992).
Veikkola et al., "Signalling via vascular endothelial growth factor receptor-3 is sufficient for lymphangiogenesis in transgenic mice," *EMBO J.* 20:1223-1231 (2001).
Wen, et al., "PTEN controls tumor-induced angiogenesis," *Proc. Natl. Acad. Sci. USA* 98 (8): 4622-4627 (2001).
Wender et al., "The design, synthesis, and evaluation of molecules that enable or enhance cellular uptake: Peptoid molecular transporters," *Proc. Natl. Acad. Sci.* 97:13003-13008 (2000).
White et al., "Antibody-targeted immunotherapy for treatment of malignancy," *Annu. Rev. Med.* 52:125-145 (2001).
Wigle and Oliver, "Prox1 function is required for the development of the murine lymphatic system," *Cell* 98:769-778 (1999).

\* cited by examiner

PEPTIDES THAT HOME TO TUMOR LYMPHATIC VASCULATURE AND METHODS OF USING SAME

This application is a continuation of U.S. Ser. No. 10/290,385, filed Nov. 5, 2002, now U.S. Pat. No. 7,192,921, which is based on, and claims the benefit of U.S. Provisional Application No. 60/421,145 filed Nov. 8, 2001, which was converted from U.S. Ser. No. 10/007,792, and each of which is incorporated herein by reference.

This invention was made with government support under CA 74238, CA 82715 and Cancer Center Support Grant CA 30199 awarded by the National Cancer Institute. The government has certain rights in this invention.

BACKGROUND OF THE INVENTION

1. Field of the Invention

The present invention relates generally to the fields of molecular medicine and drug delivery and, more specifically, to molecules that selectively home to the lymphatic vasculature of specific tumors.

2. Background Information

Metastasis, the spreading of cancer from a primary site to a secondary site often in another organ, contributes significantly to cancer patient mortality. Metastasis occurs commonly, for example, in breast cancer and in the middle and later stages of bone cancer. Most often, systemic chemotherapy is necessary to manage cancer metastasis or to diminish the likelihood that metastasis will occur. However, undesirable side effects such as severe nausea, vomiting, neuropathy, hair loss and drop in blood cell count can occur upon systemic treatment with a chemotherapeutic agent and significantly impact the quality of patient life. In addition, such undesirable side effects often limit the amount of a treatment that can be safely administered, thereby reducing cancer patient survival rates.

Cancers metastasize through tumor vasculature, which is diverse in both its cellular and molecular compositions, exhibiting variation in the type of cells that line the vessels and their complement of cell-surface receptors. Blood vessels are one type of tumor vasculature, and archetypal blood vessels are entirely lined with endothelial cells. Tumor blood vessels also can be mosaic or lined by both endothelial and tumor cells, while other vessels are formed entirely from tumor cells. Lymphatic vessels, which also occur within several tumor types, are a second type of tumor vasculature. The lymphatic vasculature is an important route for the spreading of cancer, and animal experiments have shown a positive correlation between metastasis and the number of lymphatic vessels in and around a tumor.

In view of the undesirable side effects that limit conventional systemic chemotherapy designed to reduce or prevent metastasis, there is a need for molecules which selectively home to tumor lymphatic vasculature and which are suitable, for example, for selectively targeting agents to ablate tumor lymphatic vasculature, thereby reducing the risk of tumor metastasis. The present invention satisfies this need by providing molecules that selectively home to tumor lymphatic vasculature, for example, to breast cancer and osteosarcoma lymphatic vasculature. Related advantages also are provided.

SUMMARY OF THE INVENTION

The present invention provides an isolated peptide or peptidomimetic containing the amino acid sequence GNKRTRG (SEQ ID NO: 2), or a peptidomimetic thereof. The invention further provides an isolated peptide or peptidomimetic containing the amino acid sequence CGNKRTRGC (SEQ ID NO: 1) or a peptidomimetic thereof. A peptide or peptidomimetic of the invention can be, for example, cyclic or otherwise conformationally constrained and can have a variety of lengths, for example, a length of less than 100 residues, a length of less than 50 residues, a length less than 20 residues, or a length of less than 15 residues.

The present invention further provides a conjugate containing a moiety linked to a homing molecule that selectively homes to tumor lymphatic vasculature. In one embodiment, the conjugate contains a homing molecule which selectively homes to tumor lymphatic vasculature other than melanoma vasculature. In another embodiment, the conjugate contains a homing molecule which selectively homes to tumor lymphatic vasculature and which is not an anti-VEGFR-3 or anti-LYVE-1 antibody or antigen-binding fragment thereof. In a further embodiment, the conjugate contains a homing molecule which selectively homes to tumor lymphatic vasculature and which is not an antibody or antigen-binding fragment thereof.

In a conjugate of the invention, the homing molecule that selectively homes to tumor lymphatic vasculature can be, for example, a peptide or peptidomimetic. In one embodiment, the peptide or peptidomimetic portion of the conjugate has a length of at most 200 residues. In another embodiment, the peptide or peptidomimetic portion of the conjugate has a length of at most 50 residues. In further embodiments, the conjugate contains a cyclic or otherwise conformationally constrained homing molecule, such as a peptide or peptidomimetic, that selectively homes to tumor lymphatic vasculature.

A homing molecule useful in a conjugate of the invention can be, for example, a homing peptide or peptidomimetic containing the amino acid sequence GNKRTRG (SEQ ID NO: 2), or a conservative variant or peptidomimetic thereof. If desired, such a peptide or peptidomimetic can be cyclic or otherwise conformationally constrained. A homing molecule useful in a conjugate of the invention also can be, for example, a homing peptide or peptidomimetic containing the amino acid sequence CGNKRTRGC (SEQ ID NO: 1), or a conservative variant or peptidomimetic thereof. In specific embodiments, such a homing peptide or peptidomimetic is cyclic or otherwise conformationally constrained. A variety of moieties are useful in a conjugate of the invention including, without limitation, therapeutic agents, cancer chemotherapeutic agents, cytotoxic agents, anti-lymphangiogenic agents, detectable labels and phage.

If desired, a conjugate of the invention can contain multiple homing molecules which each selectively homes to tumor lymphatic vasculature. In one embodiment, a conjugate of the invention contains at least two homing molecules which each selectively homes to tumor lymphatic vasculature. In further embodiments, a conjugate of the invention contains at least 10 homing molecules, or at least 100 homing molecules, which each selectively homes to tumor lymphatic vasculature. In another embodiment, the invention provides a conjugate containing a phage linked to at least 100 homing molecules which each selectively homes to tumor lymphatic vasculature. In a further embodiment, the invention provides a conjugate in which a phage or other particle that is linked to at least 100, 200, 300, 400 or 500 identical or non-identical homing molecules which each selectively homes to tumor lymphatic vasculature A conjugate of the invention can contain, for example, a moiety linked to at least two homing molecules which each selectively homes to tumor lymphatic vasculature and which each independently includes the amino acid sequence GNKRTRG (SEQ ID NO: 2), or a conservative variant or peptidomimetic thereof. In a further embodiment, the invention provides a conjugate containing a moiety linked to at least ten homing molecules which each selectively homes to tumor lymphatic vasculature and which each independently includes the amino acid sequence GNKRTRG (SEQ ID NO: 2) or a conservative variant or peptidomimetic thereof. In yet another embodiment, the invention provides a conjugate containing a moiety linked to at least 100 homing molecules which each selectively homes to tumor lymphatic vasculature and which each independently includes the amino acid sequence GNKRTRG (SEQ ID NO: 2) or a conservative variant or peptidomimetic thereof. Moieties useful in a conjugate of the invention containing multiple homing molecules include, but are not limited to, phage moieties.

The present invention also provides a method of directing a moiety to tumor lymphatic vasculature in a subject by administering to the subject a conjugate which contains a moiety linked to a homing molecule that selectively homes to tumor lymphatic vasculature, thereby directing the moiety to tumor lymphatic vasculature. In a method of the invention, the homing molecule can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide that contains the amino acid sequence CGNKRTRGC (SEQ ID NO: 1), or a conservative variant or peptidomimetic thereof. A variety of moieties are useful in a method of the invention including, for example, therapeutic agents, cancer chemotherapeutic agents, cytotoxic agents, anti-lymphangiogenic agents, detectable labels and phage.

The present invention also provides a method of imaging tumor lymphatic vasculature in a subject by administering to the subject a conjugate which contains a detectable label linked to a homing molecule that selectively homes to tumor lymphatic vasculature, and detecting the conjugate, thereby imaging the tumor lymphatic vasculature. In a method of the invention for imaging tumor lymphatic vasculature, the homing peptide can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide containing the amino acid sequence CGNKRTRGC (SEQ ID NO: 1), or a conservative variant or peptidomimetic thereof. A detectable label useful in an imaging method of the invention can be, for example, a radionuclide or a fluorescent molecule. Examples of radionuclides useful as detectable labels include, but are not limited to, indium-111, technetium-99, carbon-11, and carbon-13.

Further provided by the invention is a method of reducing or inhibiting tumor metastasis in a subject by administering to the subject a conjugate which contains a moiety linked to a homing molecule that selectively homes to tumor lymphatic vasculature, thereby reducing or inhibiting tumor metastasis. In a method of the invention for reducing or inhibiting tumor metastasis, the homing molecule can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide containing the amino acid sequence CGNKRTRGC (SEQ ID NO: 1), or a conservative variant or peptidomimetic thereof. A variety of moieties are useful in a method of the invention for reducing or inhibiting tumor metastasis. Such a moieties include, without limitation, cancer chemotherapeutic agents, cytotoxic agents and anti-lymphangiogenic agents.

The present invention further provides a method of reducing the number of tumor lymphatic vessels in a subject by administering to the subject a conjugate which contains a moiety linked to a homing molecule that selectively homes to tumor lymphatic vasculature, thereby reducing the number of tumor lymphatic vessels in the subject. In a method of the invention, the homing molecule can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide containing the amino acid sequence CGNKRTRGC (SEQ ID NO: 1), or a conservative variant or peptidomimetic thereof. A variety of moieties can be useful in a method of the invention for reducing the number of tumor lymphatic vessels including, without limitation, cancer chemotherapeutic agents, cytotoxic agents and anti-lymphangiogenic agents.

The present invention additionally provides a method of treating cancer in a subject by administering to the subject a conjugate which contains a moiety linked to a homing molecule that selectively homes to tumor lymphatic vasculature. In a method of the invention, the homing molecule can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide containing the amino acid sequence CGNKRTRGC (SEQ ID NO: 1), or a conservative variant or peptidomimetic thereof. A variety of moieties can be useful in a method of the invention for treating cancer in a subject including, but not limited to, cancer chemotherapeutic agents, cytotoxic agents and anti-lymphangiogenic agents.

BRIEF DESCRIPTION OF THE DRAWINGS

This patent or application file contains at least one color photograph. Copies of this patent or patent application publication with the color photographs will be provided by the Patent & Trademark Office upon request and payment of the necessary fee.

DETAILED DESCRIPTION OF THE INVENTION

Figure 1A:
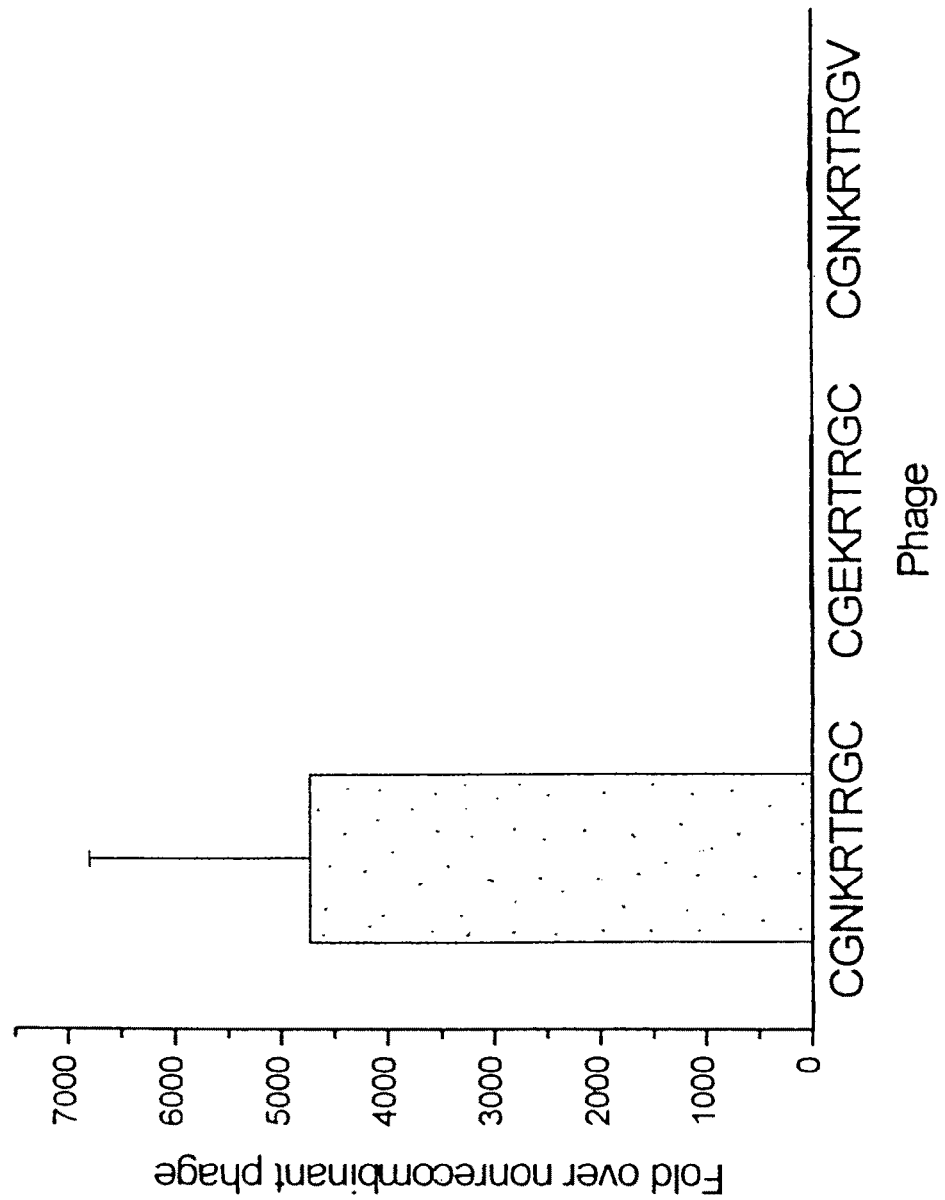
FIG. 1 shows ex vivo binding and in vivo homing of phage displaying CGNKRTRGC (SEQ ID NO: 1). (A) Binding of recombinant T7 phage displaying CGNKRTRGC (SEQ ID NO: 1), CGEKRTRGC (SEQ ID NO: 3) or CGNKRTRGV (SEQ ID NO: 4) to primary MDA-MB-435 breast carcinoma tumor cell suspensions prepared from 435 breast carcinoma xenografts. (B) Correlation of ex vivo binding of CGNKRTRGC (SEQ ID NO: 1)-displaying phage with peptide copy number displayed. (C) In vivo homing of CGNKRTRGC (SEQ ID NO: 1) phage to MDA-MB-435 breast carcinoma and KRIB osteosarcoma xenografts. (D) In vivo homing to normal tissues (normal kidney, lung, spleen, skin or breast tissue). (E) Internalization of CGNKRTRGC (SEQ ID NO: 1) phage by MDA-MB-435 breast carcinoma tumor cells.

The present invention is directed, in part, to the discovery of homing molecules which selectively home to tumor lymphatic vasculature, for example, the lymphatic vasculature of breast cancer tumors and osteosarcomas, in preference to normal lymphatic vasculature. A homing molecule of the invention also can selectively home, for example, to the lymphatic vasculature of squamous carcinomas. As disclosed herein, peptide CGNKRTRGC (SEQ ID NO: 1) was identified by a combination of ex vivo and in vivo selection as selectively homing to the lymphatic vasculature of several tumors in preference to the lymphatic vasculature of a variety of normal tissues. As shown in FIG. 1A, about 5000 times more CGNKRTRGC (SEQ ID NO: 1)-displaying phage than nonrecombinant control T7 phage bound to tumor cell suspensions prepared from MDA-MB-435 breast tumor xenografts. The CGNKRTRGC (SEQ ID NO: 1) phage also bound to tumor cell suspensions prepared from KRIB human osteosarcoma xenografts but not to C8161 melanoma or HL-60 human leukemia cells (see Example I).

Figure 1B:
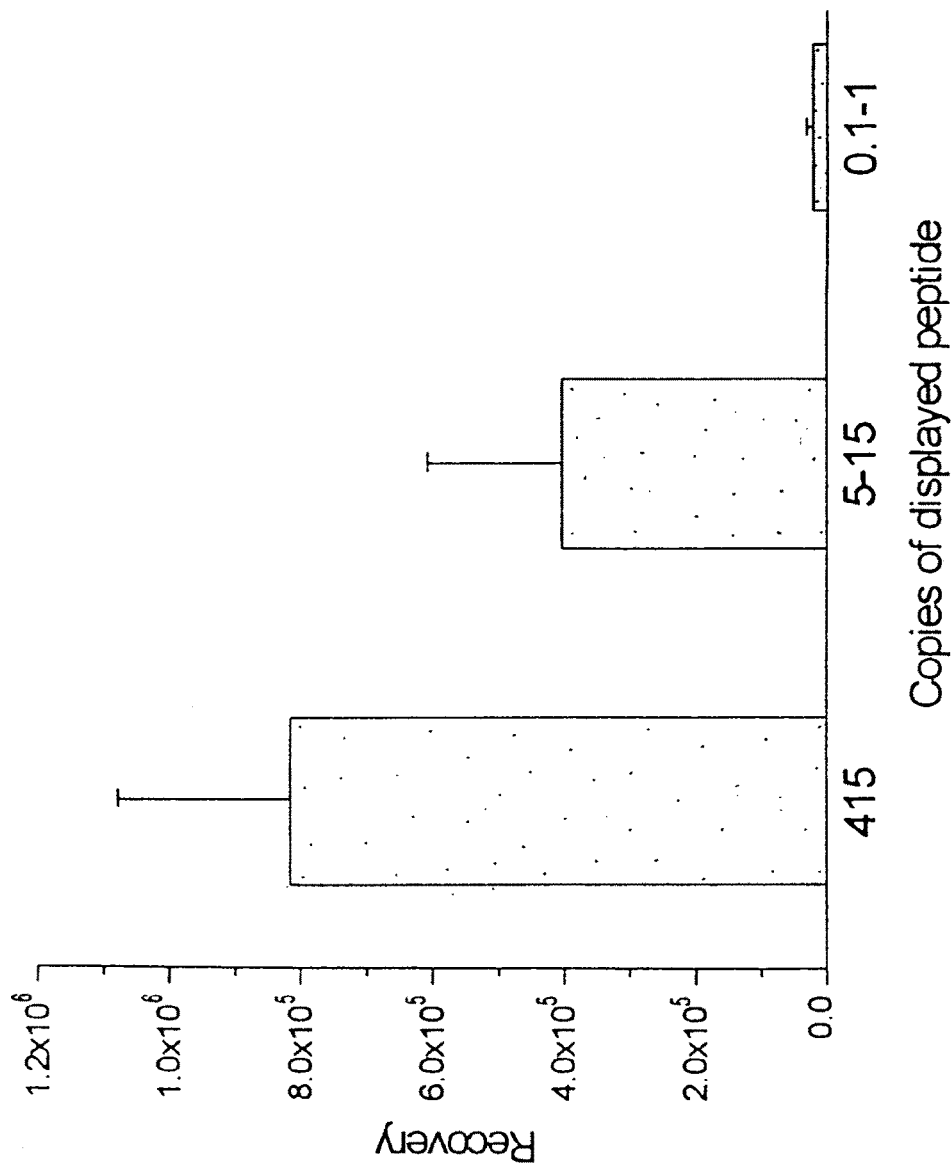
Figure 1C:
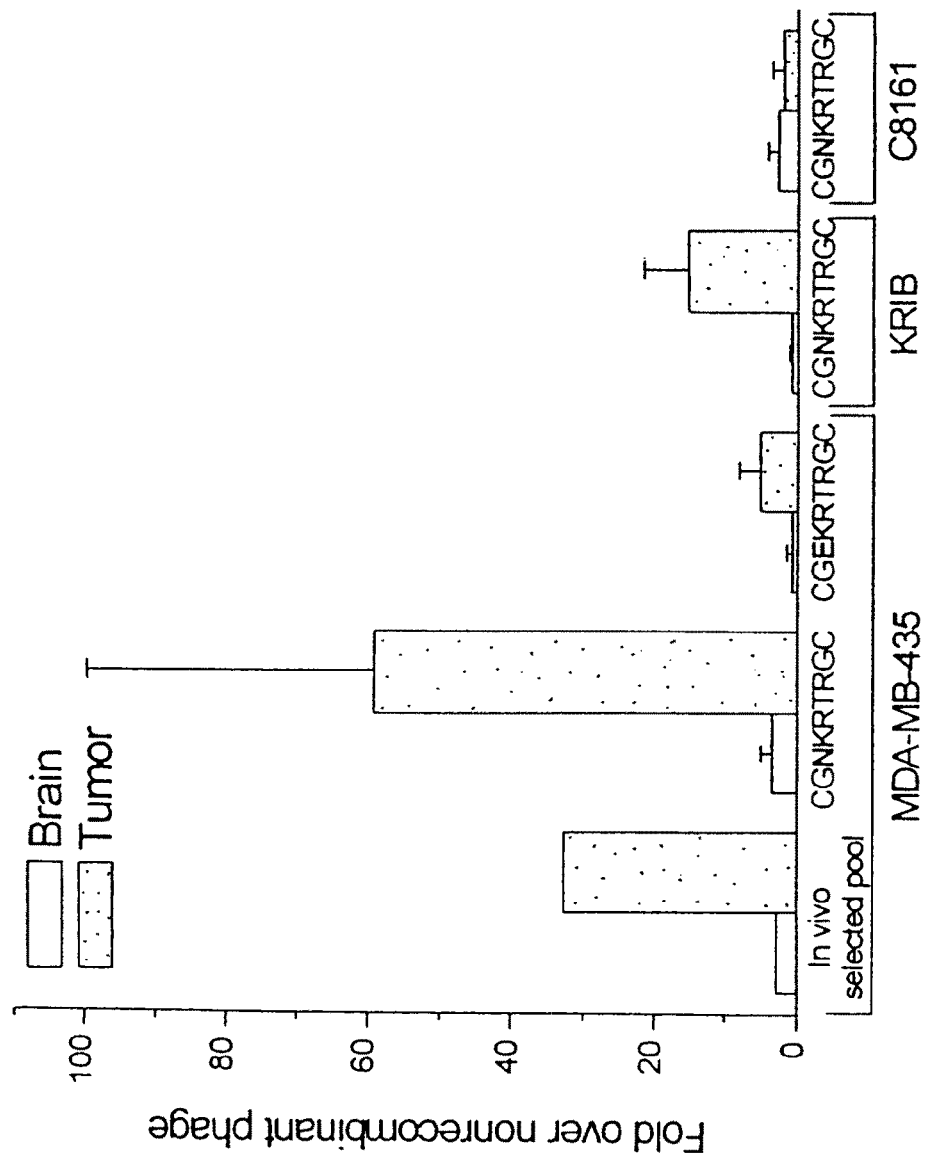
Figure 1D:
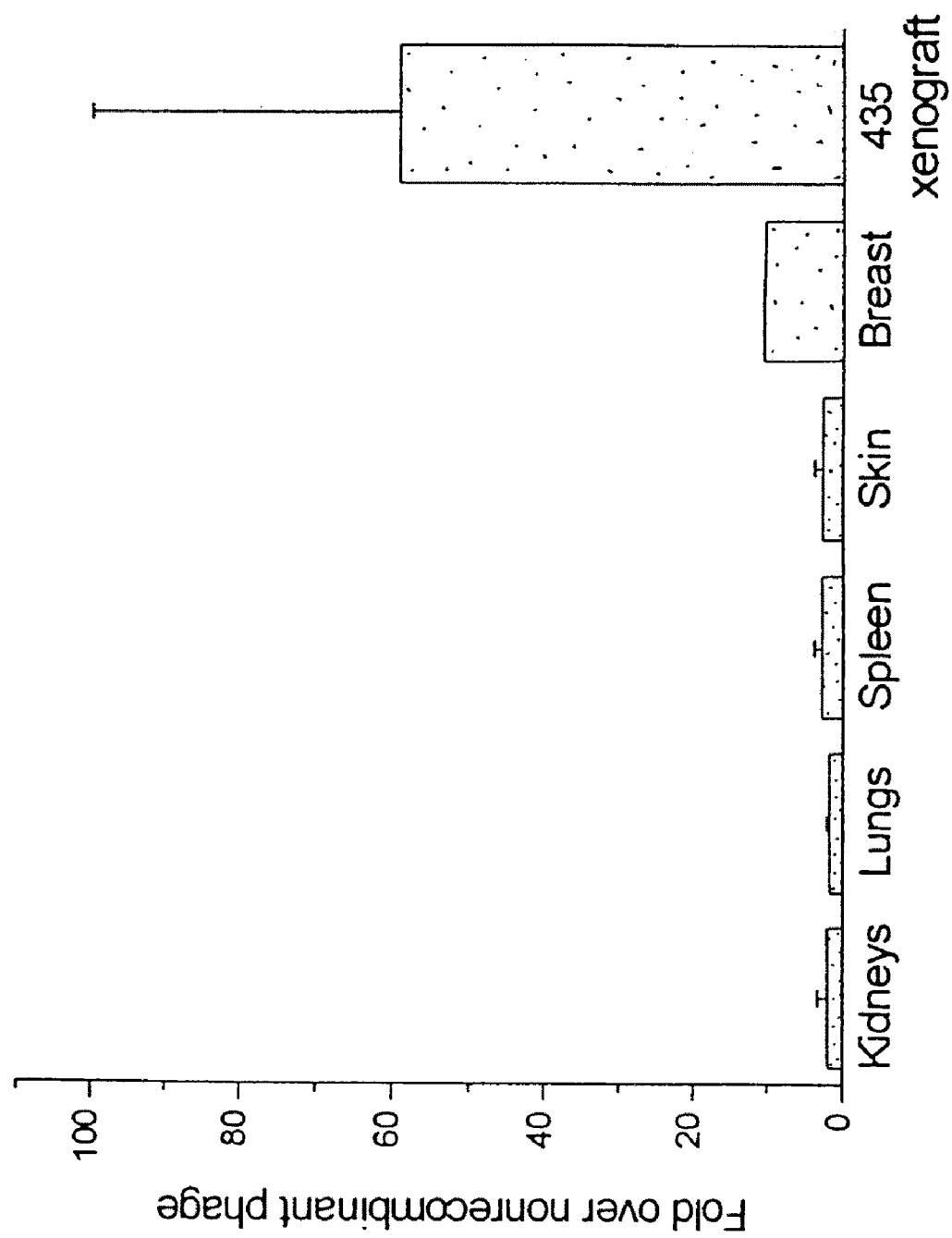

As further disclosed herein in Example 2, the CGNKRTRGC (SEQ ID NO: 1) phage selectively homed to MDA-MB-435 breast tumor and KRIB osteosarcomas in vivo. As shown in FIG. 1C, the mean phage titer of CGNKRTRGC (SEQ ID NO: 1)-displaying phage was about 60-fold greater than that of nonrecombinant phage recovered from 435 breast tumors and was 15-fold greater than that of nonrecombinant control T7 phage recovered from KRIB osteosarcomas. Furthermore, the CGNKRTRGC (SEQ ID NO: 1)-displaying phage did not home to tumors obtained with a melanoma (C8161) or leukemia (HL-60) cell line, or to a variety of normal tissues including kidney, lung, spleen, and skin, and displayed minimal affinity for normal breast tissue (see FIGS. 1C and 1D).

Figure 1E:
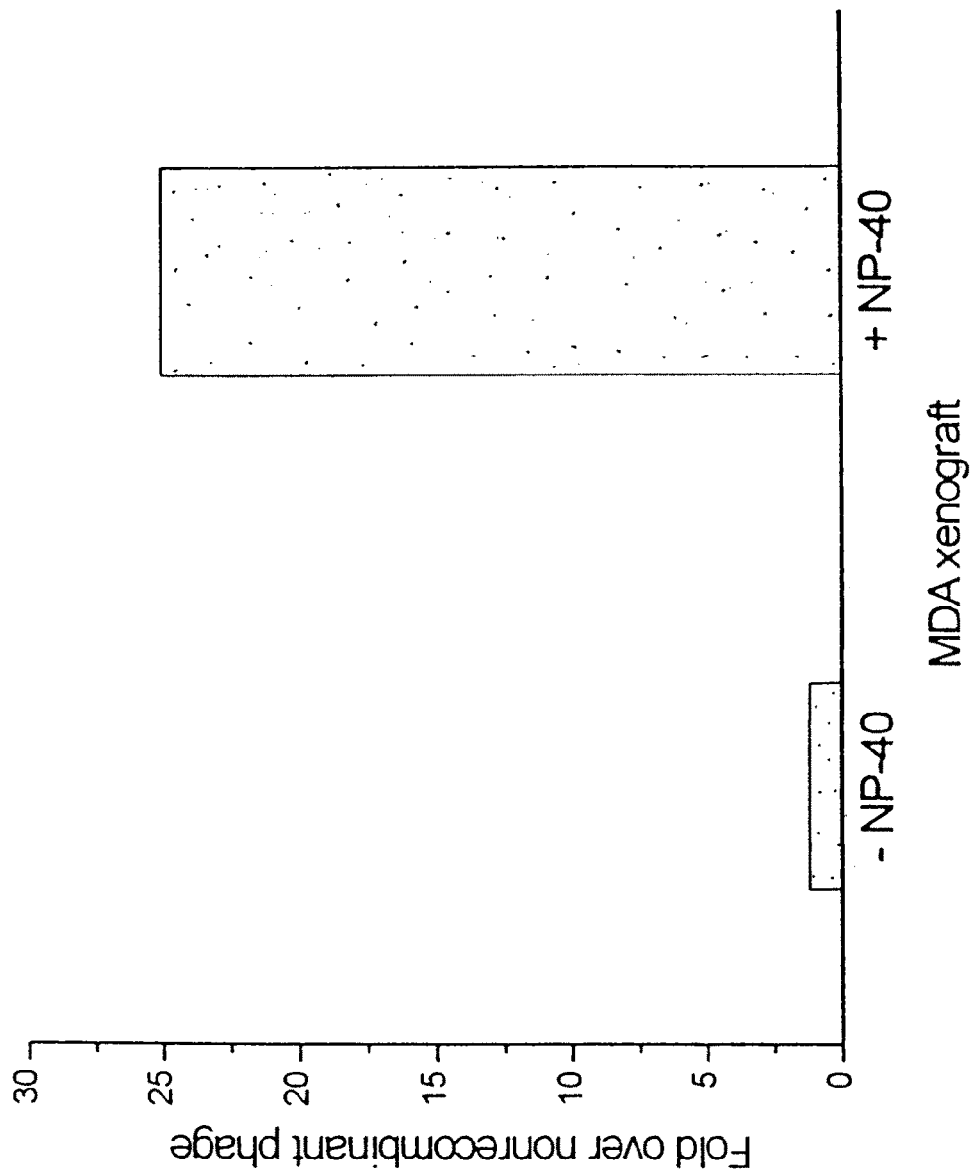
Figure 2A:
FIG. 2 shows in vitro internalization and nuclear localization of fluorescein-conjugated peptide CGNKRTRGC (SEQ ID NO: 1) in 435 cells. (A) Fluorescein-conjugated CGNKRTRGC (SEQ ID NO: 1) peptide (green). Nuclei are visualized by DAPI staining (blue). (B) Fluorescein-conjugated control peptide.

As demonstrated in Example 3, the homing peptide, SEQ ID NO: 1, was internalized by cells. In particular, following injection of SEQ ID NO: 1 phage into the tail vein of a mouse bearing a MDA-MB-435 breast tumor xenograft, ten to twenty times more CGNKRTRGC (SEQ ID NO: 1)-displaying phage were recovered from tumor samples treated with NP-40 detergent, which lyses the cells, than from untreated samples, indicating that the SEQ ID NO: 1-bearing phage had been internalized (see FIG. 1E). Internalization of CGNKRTRGC (SEQ ID NO: 1)-displaying phage was confirmed by internalization of fluorescein-labeled peptide SEQ ID NO: 1 in cultured 435 cells, indicating that the tumor cells share the receptor for peptide SEQ ID NO: 1 with the lymphatic vessel cells. As shown in FIGS. 2A and B, fluorescein-conjugated SEQ ID NO: 1 was internalized and translocated to the nucleus of 435 cells, while there was no detectable internalization of a control peptide, which, like SEQ ID NO: 1, contained three basic residues. Furthermore, fluorescein-conjugated SEQ ID NO:1 also was internalized and transported into nuclei in vivo as shown in FIG. 5.

As further disclosed herein, upon injection into the tail vein of nude mice carrying an MDA-MB-435 breast tumor, both CGNKRTRGC (SEQ ID NO: 1)-displaying phage and fluorescein conjugated peptide SEQ ID NO: 1 localized to vessel-like structures and some individual cells within the breast cancer xenograft (see Example 4). The vessels in which the phage or fluorescein-conjugated peptide localized were negative for markers CD31 and Meca-32, which are expressed by blood vessel endothelial cells in preference to lymphatic endothelial cells, indicating that the vessel-like structures targeted by peptide CGNKRTRGC (SEQ ID NO: 1) were not blood vessels. As further disclosed herein in FIG. 5, fluorescein-conjugated peptide CGNKRTRGC (SEQ ID NO: 1) co-localized with the lymphatic markers VEGFR-3 and LYVE-1 in 435 tumor tissue. However, the SEQ ID NO: 1-bearing phage did not home to the C8161 melanoma xenografts, even though these xenografts contained as many VEGFR-3/LYVE-1-positive/tomato lectin negative vessels as the 435 tumors. Together, these results indicate that peptide SEQ ID NO: 1 selectively homes to VEGFR-3 and LYVE-1 positive lymphatic vessels of several different tumors. Combined with data showing that cultured 435 and KRIB cells bound SEQ ID NO: 1-bearing phage and internalized fluorescein-labeled peptide SEQ ID NO: 1, these results indicate that the CGNKRTRGC peptide (SEQ ID NO: 1) recognizes a lymphatic vessel target molecule present on tumor cells as well as lymphatic vessel cells of the same tumors. As disclosed herein, this target molecule is not significantly expressed in the lymphatic vessels of normal tissues.

Figure 7:
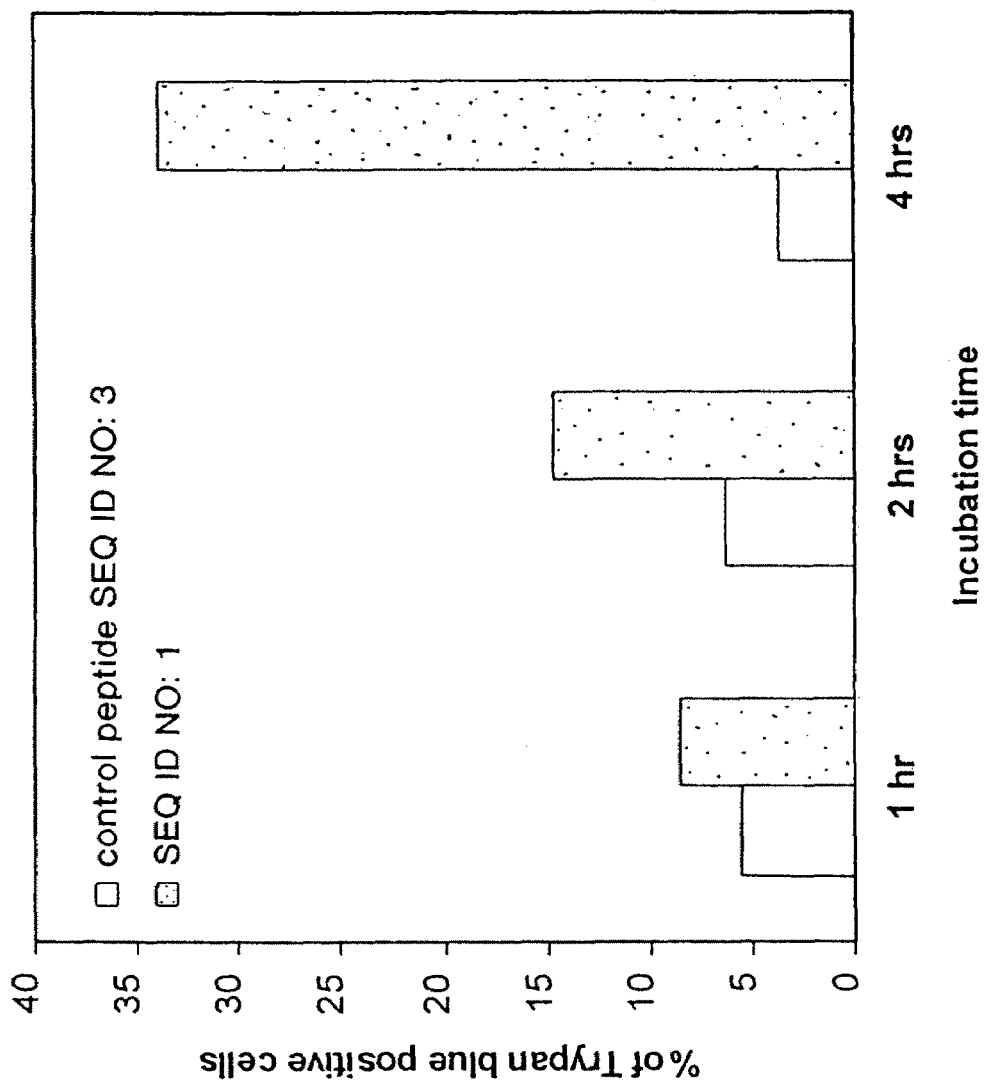
FIG. 7 shows MDA-MB-435 cells incubated with CGNKRTRGC (SEQ ID NO: 1) or with a control peptide (CGEKRTRGC; SEQ ID NO: 3). After staining with trypan blue, the total number of cells were counted, and the percentage of cells stained with trypan blue was determined.
Figure 8:
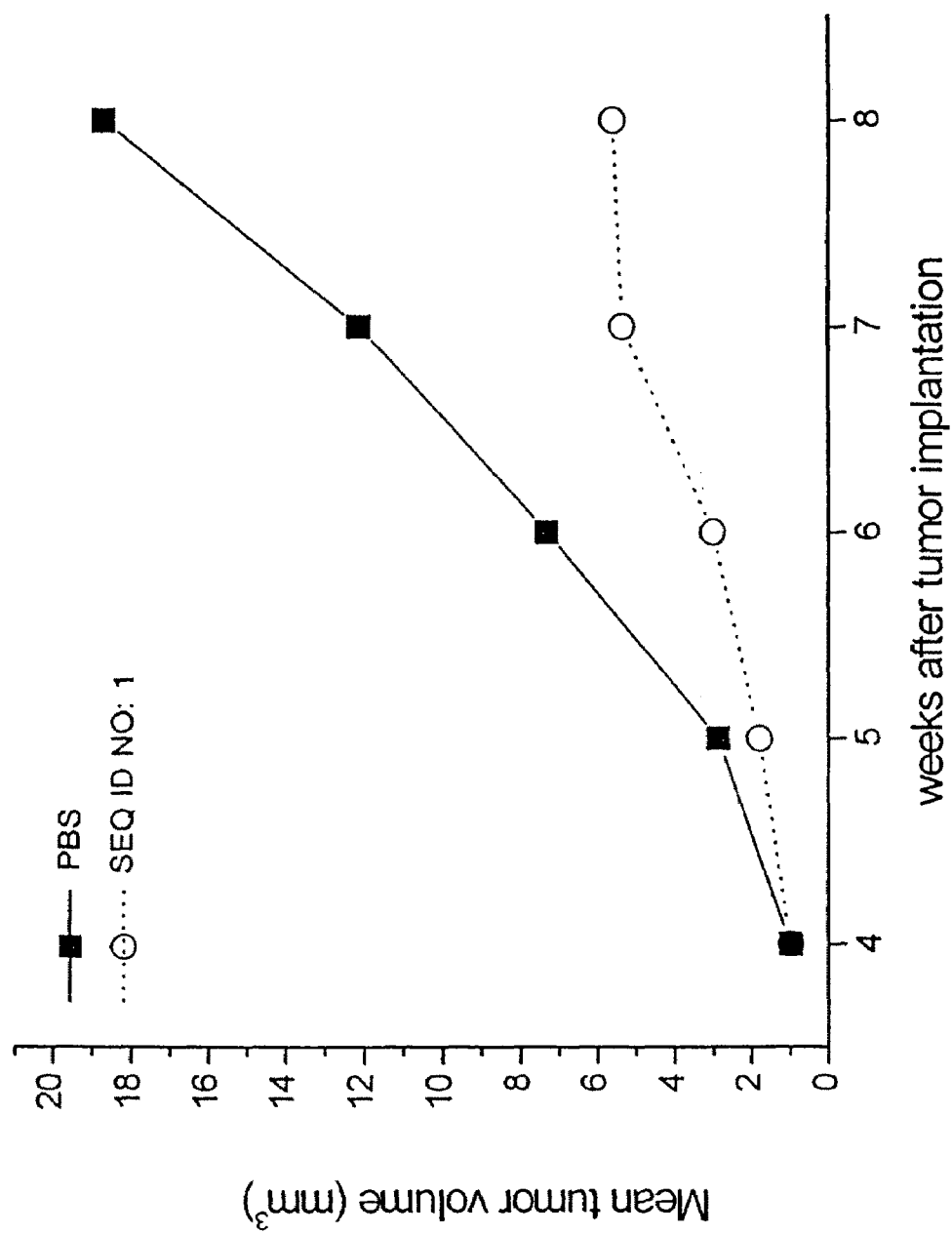
FIG. 8 shows the effect of injection of peptide CGNKRTRGC (SEQ ID NO: 1) on the growth of MDA-MB-435 human breast carcinoma xenografts in vivo.

Results disclosed herein further indicate that CGNKRTRGC peptide (SEQ ID NO: 1) has cytotoxic activity in cell culture and in vivo. As shown in FIG. 7, significantly enhanced cytotoxicity was observed in cultured MDA-MB-435 cells incubated with peptide SEQ ID NO: 1 as compared to cells incubated with control peptide. Furthermore, when MDA-MB-435 human breast carcinoma cell xenografts were treated by intravenous injection of CGNKRTRGC peptide (SEQ ID NO: 1) twice a week, tumor volumes decreased. As shown in FIG. 8, tumor growth was slowed significantly in mice treated with peptide SEQ ID NO:

1, whereas the tumor volume continued to increase rapidly in mice not treated with the peptide. These results demonstrate that peptide CGNKRTRGC (SEQ ID NO: 1) has cytotoxic activity both in cell culture and in vivo and further indicate that this peptide as well as structurally related peptides and peptidomimetics, and molecules that bind the same receptor can be useful for slowing or preventing tumor growth in vivo.

Based on these findings, the present invention provides homing molecules and conjugates useful, for example, for reducing or preventing tumor metastasis in cancer patients having a primary tumor. The conjugates of the invention can be administered, for example, to a subject having pre-metastatic breast or bone cancer or to a subject having early or late stage metastatic breast or bone cancer. Conjugates of the invention also can be useful, for example, for imaging tumor lymphatic vasculature, such as breast cancer or osteosarcoma lymphatic vasculature.

Thus, the present invention provides an isolated peptide or peptidomimetic containing the amino acid sequence GNKRTRG (SEQ ID NO: 2), or a peptidomimetic thereof. The invention further provides an isolated peptide or peptidomimetic containing the amino acid sequence CGNKRTRGC (SEQ ID NO: 1) or a peptidomimetic thereof. A peptide or peptidomimetic of the invention can be, for example, cyclic or otherwise conformationally constrained and can have a variety of lengths, for example, a length of less than 100 residues, a length of less than 50 residues, a length less than 20 residues, or a length of less than 15 residues. In one embodiment, a peptide or peptidomimetic of the invention which contains the amino acid sequence GNKRTRG (SEQ ID NO: 2) or CGNKRTRGC (SEQ ID NO: 1), or a peptidomimetic of one of these sequences, has cytotoxic activity. It is understood that a peptide containing, for example, the amino acid sequence SEQ ID NO: 1 or SEQ ID NO: 2 includes the specified amino acids as a contiguous sequence in which the specified amino acids are not separated by other amino acids.

The peptides and peptidomimetics of the invention are provided in isolated form. As used herein in reference to a peptide or peptidomimetic of the invention, the term "isolated" means a peptide or peptidomimetic that is in a form that is relatively free from material such as contaminating polypeptides, lipids, nucleic acids and other cellular material that normally is associated with the peptide or peptidomimetic in a cell or that is associated with the peptide or peptidomimetic in a library or in a crude preparation.

The peptides and peptidomimetics of the invention, including the bifunctional, multivalent and homing peptides and peptidomimetics discussed below, can have a variety of lengths. A peptide or peptidomimetic of the invention can have, for example, a relatively short length of less than eight, nine, ten, 12, 15, 20, 25, 30, 35 or 40 residues. A peptide or peptidomimetic of the invention also can be useful in the context of a significantly longer sequence. For example, as disclosed herein, peptide CGNKRTRGC (SEQ ID NO: 1) maintained the ability to home when fused to a phage coat protein, confirming that a peptide of the invention can have selective homing activity when embedded in larger protein sequence. Thus, a peptide or peptidomimetic of the invention can have, for example, a length of up to 50, 100, 150 or 200 residues. As used herein, the term "residue" refers to amino acids or analogs thereof.

The present invention also provides an isolated peptide or peptidomimetic containing the amino acid sequence GNKRTRG (SEQ ID NO: 2) or CGNKRTRGC (SEQ ID NO: 1), or a conservative variant or peptidomimetic of one of these sequences. As used herein, a "conservative variant" is an amino acid sequence in which a first amino acid is replaced by a second amino acid or amino acid analog having at least one similar biochemical property, which can be, for example, similar size, charge, hydrophobicity or hydrogen-bonding capacity. For example, a first hydrophobic amino acid can be conservatively substituted with a second (non-identical) hydrophobic amino acid such as alanine, valine, leucine, or isoleucine, or an analog thereof. Similarly, a first basic amino acid can be conservatively substituted with a second basic amino acid such as arginine or lysine, or an analog thereof. In the same way, a first acidic amino acid can be conservatively substituted with a second acidic amino acid such as aspartic acid or glutamic acid, or an analog thereof, or an aromatic amino acid such as phenylalanine can be conservatively substituted with a second aromatic amino acid or amino acid analog, for example, tyrosine.

The invention further provides a chimeric protein containing a peptide or peptidomimetic of the invention, or a homing peptide or peptidomimetic of the invention, fused to a heterologous protein. In one embodiment, the invention provides a chimeric protein containing a homing peptide or peptidomimetic that selectively homes to tumor lymphatic vasculature fused to a heterologous protein. In one embodiment, the homing peptide or peptidomimetic that selectively homes to tumor lymphatic vasculature has cytotoxic activity. In another embodiment, the heterologous protein has a therapeutic activity. In a further embodiment, the heterologous protein is an antibody or antigen-binding fragment thereof. In other embodiments, the invention provides a chimeric protein in which a peptide or peptidomimetic containing the amino acid sequence CGNKRTRGC (SEQ ID NO: 1) or GNKRTRG (SEQ ID NO: 2), or a conservative variant or peptidomimetic of one of these sequences, is fused to a heterologous protein. The term "heterologous," as used herein in reference to a protein fused to a peptide or peptidomimetic of the invention, means a protein derived from a source other than the gene encoding the peptide of the invention or upon which the peptidomimetic is derived. A chimeric protein of the invention can have a variety of lengths, for example, up to 100, 200, 300, 400, 500 or 800 residues.

The invention also provides a bifunctional peptide which contains a homing peptide that selectively homes to tumor lymphatic vasculature, such as the lymphatic vasculature of breast cancers or osteosarcomas, fused to a second peptide having a separate function. Such bifunctional peptides have at least two functions conferred by different portions of the peptide and can, for example, display anti-lymphangiogenic activity or pro-apoptotic activity in addition to selective homing activity. As exemplary bifunctional peptides, the invention provides CGNKRTRGC-GG-$_D$(KLAKLAK)$_2$ and GNKRTRG-GG-$_D$(KLAKLAK)$_2$. In such peptides, the CGNKRTRGC (SEQ ID NO: 1) portion exhibits selective homing activity and cytotoxic activity, while the $_D$(KLAKLAK)$_2$ portion exhibits pro-apoptotic activity.

The present invention further provides an isolated multivalent peptide or peptidomimetic that includes at least two motifs each independently containing the amino acid sequence GNKRTRG (SEQ ID NO: 2), or a conservative variant or peptidomimetic thereof. The multivalent peptide or peptidomimetic can have, for example, at least three, at least five or at least ten of such motifs each independently containing the amino acid sequence GNKRTRG (SEQ ID NO: 2), or a conservative variant or peptidomimetic thereof. In particular embodiments, the multivalent peptide or peptidomimetic has two, three, four, five, six, seven, eight, nine, ten, fifteen or twenty identical or non-identical motifs of the amino acid sequence GNKRTRG (SEQ ID NO: 2), or a conservative variant or peptidomimetic thereof. In another embodiment, the multivalent peptide or peptidomimetic contains identical motifs, which consist of the amino acid sequence SEQ ID NO: 2, or conservative variants or peptidomimetics thereof. In a further embodiment, the multivalent peptide or peptidomimetic contains contiguous motifs, which are not separated by any intervening amino acids. In yet further embodiments, the multivalent peptide or peptidomimetic is cyclic or otherwise conformationally constrained, or has cytotoxic activity.

In an isolated multivalent peptide or peptidomimetic of the invention, at least one motif can be, if desired, CGNKRTRGC (SEQ ID NO: 1), or a conservative variant or peptidomimetic thereof. In particular embodiments, a multivalent peptide or peptidomimetic of the invention has two, three, four, five, six, seven, eight, nine, ten, fifteen or twenty identical or non-identical motifs of the amino acid sequence CGNKRTRGC (SEQ ID NO: 1), or a conservative variant or peptidomimetic thereof. Such multivalent peptides or peptidomimetics can be, if desired, contiguous and further can be, if desired, cyclic or otherwise conformationally constrained.

Thus, the invention provides peptides and peptidomimetics, including bifunctional and multivalent peptides and peptidomimetics, and homing peptides and peptidomimetics discussed further below. As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective homing activity of the peptide upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^α$—$C^α$ cyclized amino acid; an $N^α$-methylated amino acid; a β- or γ-amino cycloalkane carboxylic acid; an α,α-unsaturated amino acid; a β,β-dimethyl or β-methyl amino acid; a β-substituted-2,3-methano amino acid; an N—$C^δ$ or $C^α$—$C^δ$ cyclized amino acid; a substituted proline or another amino acid mimetic. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., *Acta Crystallogr.* Section B, 35:2331 (1979)). This structural depository is continually updated as new crystal structures are determined and can be screened for compounds having suitable shapes, for example, the same shape as a peptide of the invention, as well as potential geometrical and chemical complementarity to a target molecule. Where no crystal structure of a peptide of the invention or a target molecule that binds the peptide is available, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide of the invention, for example, with activity in selectively homing to tumor lymphatic vasculature.

An isolated peptide or peptidomimetic of the invention, or a homing molecule of the invention as discussed further below, can be cyclic, or otherwise conformationally constrained. As used herein, a "conformationally constrained" molecule, such as a peptide or peptidomimetic, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization.

In one embodiment, a peptide or peptidomimetic of the invention, or a homing molecule such as a homing peptide or peptidomimetic, is cyclic. As used herein, the term "cyclic" refers to a molecule having non-adjacent components linked to one another through a covalent or ionic bond or through an equivalent interaction such that a rigid or semi-rigid three dimensional structure of the molecule is maintained.

As used herein in reference to a peptide or peptidomimetic, the term cyclic refers to a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof (see, also, Table 1).

TABLE 1

AMINO ACIDS AND AMINO ACID ANALOGS USEFUL FOR CYCLIZATION

| AMINO ACID* | THREE LETTER CODE | TYPE OF BOND |
|---|---|---|
| γ-amino-adipic acid | Adp | Lactam |
| Aspartic acid | Asp | Lactam |
| Cysteine | Cys | Disulfide |
| Glutamic acid | Glu | Lactam |
| Leucine | Leu | Lysinonorleucine |
| Lysine | Lys | Lactam and Lysinonorleucine |
| -(aminomethyl)benzoic acid | Mamb | Lactam |
| Ornithine | Orn | Lactam |
| Penicillamine | Pen | Disulfide |

TABLE 1-continued

AMINO ACIDS AND AMINO ACID ANALOGS
USEFUL FOR CYCLIZATION

| AMINO ACID* | THREE LETTER CODE | TYPE OF BOND |
|---|---|---|
| α,β-diaminopropionic acid | — | Lactam |
| β,β-pentamethylene cysteine | Pmc | Disulfide |
| β,β-pentamethylene-β-mercaptopropionic acid | Pmp | Disulfide |
| Tyrosine | Tyr | Dityrosine |

-includes ammo acids and analogs thereof.

A peptide or peptidomimetic also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (Orn), α,β-diaminopropionic acid, γ-amino-adipic acid (Adp) and M-(aminomethyl)benzoic acid (Mamb). Cyclization additionally can be effected, for example, through the formation of a lysinonorleucine bond between lysine (Lys) and leucine (Leu) residues or a dityrosine bond between two tyrosine (Tyr) residues.

The present invention also provides an isolated homing peptide or peptidomimetic that selectively homes to tumor lymphatic vasculature. In one embodiment, the isolated homing peptide or peptidomimetic selectively homes to tumor lymphatic vasculature other than melanoma vasculature. In another embodiment, the isolated homing peptide or peptidomimetic is not an anti-VEGFR-3 or anti-LYVE-1 antibody or antigen-binding fragment thereof. In a further embodiment, the isolated homing peptide or peptidomimetic is not an antibody or antigen-binding fragment thereof. An isolated homing peptide or peptidomimetic of the invention can include, for example, the amino acid sequence GNKRTRG (SEQ ID NO: 2) or the amino acid sequence CGNKRTRGC (SEQ ID NO: 1), or a conservative variant or peptidomimetic of one of these sequences.

The present invention further provides a conjugate which contains a moiety linked to a homing molecule that selectively homes to tumor lymphatic vasculature. In one embodiment, the conjugate contains a homing molecule which selectively homes to tumor lymphatic vasculature other than melanoma vasculature. In another embodiment, the conjugate contains a homing molecule which selectively homes to tumor lymphatic vasculature and which is not an anti-VEGFR-3 or anti-LYVE-1 antibody or antigen-binding fragment thereof. In a further embodiment, the conjugate contains a homing molecule which selectively homes to tumor lymphatic vasculature and which is not an antibody or antigen-binding fragment thereof. In yet a further embodiment, the conjugate contains a homing molecule which selectively homes to tumor lymphatic vasculature and which has cytotoxic activity.

In a conjugate of the invention, the homing molecule that selectively homes to tumor lymphatic vasculature can be, for example, a peptide or peptidomimetic. In one embodiment, the peptide or peptidomimetic portion of the conjugate has a length of at most 200 residues. In another embodiment, the peptide or peptidomimetic portion of the conjugate has a length of at most 50 residues. In further embodiments, the conjugate contains a cyclic or otherwise conformationally constrained homing molecule, such as a peptide or peptidomimetic, that selectively homes to tumor lymphatic vasculature. In yet further embodiments, the peptide or peptidomimetic portion of the conjugate has cytotoxic activity.

A homing molecule useful in a conjugate of the invention can be, for example, a homing peptide or peptidomimetic containing the amino acid sequence GNKRTRG (SEQ ID NO: 2), or a conservative variant or peptidomimetic thereof. If desired, such a peptide or peptidomimetic can be cyclic or otherwise conformationally constrained. A homing molecule useful in a conjugate of the invention also can be, for example, a homing peptide or peptidomimetic containing the amino acid sequence CGNKRTRGC (SEQ ID NO: 1), or a conservative variant or peptidomimetic thereof. In specific embodiments, such a homing peptide or peptidomimetic is cyclic or otherwise conformationally constrained. A variety of moieties are useful in a conjugate of the invention including, without limitation, therapeutic agents, cancer chemotherapeutic agents, cytotoxic agents, anti-lymphangiogenic agents, detectable labels and phage.

As disclosed herein, peptide SEQ ID NO: 1 recognizes a lymphatic vessel target "receptor" which is expressed on some tumor cells as well as lymphatic vessel cells of the same tumors but which is not significantly expressed in the lymphatic vessels of normal tissues. The binding of SEQ ID NO: 1 to this target receptor forms the basis for the selective homing activity of peptide SEQ ID NO: 1 and related peptides and peptidomimetics. Based on this discovery, it is clear that molecules structurally unrelated to SEQ ID NO: 1 but which bind the same target receptor also have the same characteristic of selective homing to tumor lymphatic vasculature. Such molecules can be identified by the ability to specifically bind to, or compete for binding to, the target receptor bound by SEQ ID NO: 1. Thus, the invention provides a molecule that specifically binds the receptor bound by peptide SEQ ID NO: 1; such a molecule also is characterized by the ability to selectively home to tumor lymphatic vasculature. In one embodiment, the molecule is a peptide or peptidomimetic, which can have, for example, a length of at most 20, 50 or 200 residues.

The invention also provides a conjugate which contains a moiety linked to a molecule that specifically binds the receptor bound by peptide SEQ ID NO: 1 and that selectively homes to tumor lymphatic vasculature. In such a conjugate, the molecule can be, for example, a peptide or peptidomimetic, and the moiety can be any of the moieties disclosed herein as useful in the conjugates of the invention.

The present invention also provides a method of directing a moiety to tumor lymphatic vasculature in a subject by administering to the subject a conjugate which contains a moiety linked to a homing molecule that selectively homes to tumor lymphatic vasculature, thereby directing the moiety to tumor lymphatic vasculature. In one embodiment, a method of directing a moiety to tumor lymphatic vasculature is practiced with a conjugate containing a homing molecule which selectively homes to tumor lymphatic vasculature other than melanoma vasculature. In another embodiment, a method of the invention is practiced with a conjugate containing a homing molecule which selectively homes to tumor lymphatic vasculature and which is not an anti-VEGFR-3 or anti-LYVE-1 antibody or antigen-binding fragment thereof. In a further embodiment, a method of the invention is practiced with a conjugate containing a homing molecule which selectively homes to tumor lymphatic vasculature and which is not an antibody or antigen-binding fragment thereof. In yet a further embodiment, a method of the invention is practiced with a conjugate that contains a homing molecule which selectively homes to tumor lymphatic vasculature and which has cytotoxic activity.

In a method of the invention, the homing molecule can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide that contains the amino acid sequence CGNKRTRGC (SEQ ID NO: 1), or a conservative variant or peptidomimetic thereof. A variety of moieties are useful in a method of the invention including, for example, therapeutic agents, cancer chemotherapeutic agents, cytotoxic agents, anti-lymphangiogenic agents, detectable labels and phage.

It is understood that a variety of routes of administration are useful in the methods of the invention. Such routes include both systemic and local administration, including, without limitation, oral administration, intravenous injection, intraperitoneal injection, intramuscular injection, subcutaneous injection, transdermal diffusion or electrophoresis, local injection; extended release delivery devices including locally implanted extended release devices including bioerodible and reservoir-based implants.

As used herein, the term "molecule" is used broadly to mean a polymeric or non-polymeric organic chemical such as a small molecule drug; a nucleic acid molecule such as an RNA, a cDNA or an oligonucleotide; a peptide or peptidomimetic; or a protein such as an antibody or a growth factor receptor or a fragment thereof such as an Fv, Fd, or Fab fragment of an antibody containing the antigen-binding domain.

Exemplified herein are various homing molecules which selectively home to tumor lymphatic vasculature but which do not detectably home to the lymphatic vessels of several normal tissues such as CGNKRTRGC (SEQ ID NO: 1), GNKRTRG (SEQ ID NO: 2), and conservative variants or peptidomimetics thereof. Additional homing molecules that selectively home to tumor lymphatics can be identified using in vivo panning coupled, if desired, with ex vivo selection, as disclosed in Examples 1 and 2 (see, also, U.S. Pat. No. 5,622, 699).

The term "homing molecule" as used herein, means any molecule that selectively homes in vivo to the lymphatic vasculature of one or more tumors in preference to normal lymphatic vasculature. Similarly, the term "homing peptide" or "homing peptidomimetic" means a peptide or peptidomimetic that selectively homes in vivo to the lymphatic vasculature of one or more tumors in preference to normal lymphatic vasculature. It is understood that a homing molecule that selectively homes in vivo to tumor lymphatic vasculature can home to the lymphatic vasculature of all tumors or can exhibit preferential homing to the lymphatic vasculature of a subset of tumor types.

By "selectively homes" is meant that, in vivo, the homing molecule, peptide or peptidomimetic binds preferentially to tumor lymphatic vasculature, such as breast tumor or osteosarcoma lymphatic vasculature, as compared to non-tumoral lymphatic vasculature. Selective homing generally is characterized by at least a two-fold two-fold greater localization within tumor lymphatic vasculature, such as breast or osteosarcoma lymphatic vasculature as compared to several tissue types of non-tumoral lymphatic vasculature. A homing molecule can be characterized by 5-fold, 10-fold, 20-fold or more preferential localization to tumor lymphatic vasculature as compared to several tissue types of non-tumoral lymphatic vasculature, or as compared to most or all non-tumoral lymphatic vasculature. Thus, it is understood that a homing molecule can home, in part, to the lymphatic vasculature of one or more normal organs, in addition to tumor lymphatic vasculature.

In one embodiment, a conjugate of the invention includes a homing molecule that is not an antibody or antigen-binding fragment thereof, which is an art-recognized term that refers to a peptide or polypeptide containing one or more complementarity determining regions (CDRs). See, for example, Borrabaeck, *Antibody Engineering* 2nd Edition, Oxford University Press, New York (1995).

In another embodiment, the peptide or peptidomimetic portion of the conjugate has a defined length. The peptide or peptidomimetic portion of the conjugate can have, for example, a length of at most 10, 20, 30, 40, 50, 100, 150, 200, 250, 300, 400, 500, 600, 700, 800, 900, 1000 or 2000 residues. It is understood that the term "peptide or peptidomimetic portion of the conjugate" means total number of residues in the homing peptide or peptidomimetic and any contiguous protein, peptide or peptidomimetic, such as a therapeutic protein or pro-apoptotic peptide.

If desired, a conjugate of the invention can contain multiple homing molecules which each selectively homes to tumor lymphatic vasculature. In one embodiment, a conjugate of the invention contains at least two homing molecules which each selectively homes to tumor lymphatic vasculature. In further embodiments, a conjugate of the invention contains at least 10 homing molecules, or at least 100 homing molecules, which each selectively homes to tumor lymphatic vasculature. In yet a further embodiment, the invention provides a conjugate containing a phage linked to at least 100 homing molecules which each selectively homes to tumor lymphatic vasculature.

A conjugate of the invention can contain, for example, a moiety linked to at least two homing molecules which each selectively homes to tumor lymphatic vasculature and which each independently includes the amino acid sequence GNKRTRG (SEQ ID NO: 2), or a conservative variant or peptidomimetic thereof. In a further embodiment, the invention provides a conjugate containing a moiety linked to at least ten homing molecules which each selectively homes to tumor lymphatic vasculature and which each independently includes the amino acid sequence GNKRTRG (SEQ ID NO: 2) or a conservative variant or peptidomimetic thereof. In yet another embodiment, the invention provides a conjugate containing a moiety linked to at least 100 homing molecules which each selectively homes to tumor lymphatic vasculature and which each independently includes the amino acid sequence GNKRTRG (SEQ ID NO: 2) or a conservative variant or peptidomimetic thereof. Moieties useful in a conjugate of the invention containing multiple homing peptides include, but are not limited to, phage moieties.

Thus, a conjugate of the invention containing multiple homing molecules can include, for example, two or more, three or more, five or more, ten or more, twenty or more, thirty or more, forty or more, fifty or more, 100 or more, 200 or more, 300 or more, 400 or more, 500 or more or 100 or more homing molecules. In one embodiment, the homing molecules have an identical amino acid sequence. In another embodiment, the conjugate includes homing molecules having non-identical amino acid sequences. Moieties useful in a conjugate of the invention that incorporates multiple homing molecules include, without limitation, phage, retroviruses, adenoviruses, adeno-associated viruses and other viruses, cells, liposomes, polymeric matrices, non-polymeric matrices or particles such as gold particles, microdevices and nanodevices, and nano-scale semiconductor materials.

A conjugate of the invention can contain, for example, a liposome or other polymeric matrix linked to at least two homing molecules which each selectively homes to tumor lymphatic vasculature. If desired, the liposome or other polymeric matrix can be linked to at least ten or at least 100 homing molecules which each selectively homes to tumor lymphatic vasculature. Homing molecules useful in such a conjugate can independently include, for example, the amino acid sequence GNKRTRG (SEQ ID NO: 2), the amino acid sequence CGNKRTRGC (SEQ ID NO: 1), or a conservative variant or peptidomimetic of one of these sequences. Liposomes, for example, which consist of phospholipids or other lipids, are nontoxic, physiologically acceptable and metabolizable carriers that are relatively simple to make and administer (Gregoriadis, *Liposome Technology*, Vol. 1 (CRC Press, Boca Raton, Fla. (1984)). The liposome or other polymeric matrix additionally can include another component if desired, for example, a therapeutic agent, cancer chemotherapeutic agent, cytotoxic agent or anti-lymphangiogenic agent.

A conjugate of the invention includes a moiety linked to a homing molecule that selectively homes to tumor lymphatic vasculature. As used herein, the term "moiety" is used broadly to mean a physical, chemical, or biological material that can be linked to a homing molecule of the invention and generally imparts a biologically useful function to the homing molecule. A moiety can be any natural or nonnatural material including a biological material, such as a cell or phage; an organic chemical, such as a small molecule; a radionuclide; a nucleic acid molecule or oligonucleotide; a polypeptide; or a peptide or peptidomimetic. Moieties useful in the invention include, without limitation, therapeutic agents; cancer chemotherapeutic agents, cytotoxic agents, pro-apoptotic agents, anti-lymphangiogenic agents, detectable labels and imaging agents; and tags or other insoluble supports. Moieties useful in the invention further include, for example, phage and other viruses, cells, liposomes, polymeric matrices, non-polymeric matrices or particles such as gold particles, microdevices and nanodevices, and nano-scale semiconductor materials. These and other moieties known in the art can be components of a conjugate of the invention, as disclosed herein.

In one embodiment, a moiety useful in a conjugate of the invention is an anti-lymphangiogenic agent. As used herein, the term "anti-lymphangiogenic agent" is a molecule that reduces or inhibits the growth of lymphatic vessels. Stimulation of the vascular endothelial growth factor receptor-3 (VEGFR-3) signal transduction pathway is sufficient to specifically induce lymphangiogenesis in vivo, and VEGFR-3 expression mainly is restricted to lymphatic vessels in later development. Furthermore, the VEGFR-3 ligand, VEGF-C, is mitogenic towards lymphatic endothelial cells and can induce a lymphangiogenic response in differentiated avian chorioallantoic membrane and mouse skin (Karkkainen and Petrova, *Oncogene* 19:5598-5605 (2000); and Veikkola et al., *EMBO J.* 20:1223-1231 (2001)). Thus, an anti-lymphangiogenic agent can be, for example, a VEGFR-3 inhibitor, which is a molecule that inhibits VEGFR-3 expression, activity, or signaling.

A VEGFR-3 inhibitor can be selective for VEGFR-3 and can exhibit, for example, at least 10-fold greater inhibition of VEGFR-3 expression or activity as compared to the expression or activity of other vascular endothelial growth factor receptors (VEGFRs). Such a selective VEFGR-3 inhibitor can exhibit, for example, at least 20-fold, 50-fold, or 100-fold greater inhibition of VEGFR-3 expression or activity as compared to the expression or activity of other VEGFRs. It is understood that a non-selective VEGFR-3 inhibitor also can be useful in the invention. Such a VEGFR-3 inhibitor inhibits the expression or activity of one or more other VEGFRs such as VEGFR-1 or VEGFR-2 or other tyrosine kinases in addition to inhibiting VEGFR-3. It further is understood that a VEGFR-3 inhibition or other anti-lymphangiogenic agent also can have additional activity, for example, as an anti-angiogenic agent.

A variety of anti-lymphangiogenic agents are known in the art including for example, VEGFR-3 antagonists, which bind to but do not activate VEGFR-3; soluble receptors or other dominant negative VEGFR-3 receptors such as kinase-inactive receptors; inhibitory anti-VEGFR-3 antibodies; competitors of VEGFR-3 ligand binding, for example, VEGF-C or VEGF-D binding; small molecules; antisense nucleic acid molecules; ribozymes; transcription factors or their encoding nucleic acid molecules; or other molecules which reduce VEGFR-3 expression; selective VEGFR-3 kinase inhibitors such as ATP analogs; and selective inhibitors of the VEGFR-3 signaling pathway. Thus, it is understood that various types of molecules can function as an anti-lymphangiogenic agent, including a small molecule; a protein, for example, a dominant negative receptor, transcription factor or antibody; a peptide or peptidomimetic; a ribozyme; or a nucleic acid molecule such as an antisense oligonucleotide or nucleic acid molecule encoding a dominant negative receptor, transcription factor or antibody.

In one embodiment, a moiety contained in a conjugate of the invention is a therapeutic agent. As used herein, the term "therapeutic agent" means a molecule which alters biological activity in a normal or pathologic tissue. A therapeutic agent, therefore, is potentially useful for the treatment of disease conditions. A variety of therapeutic agents can be contained in a conjugate of the invention. In another embodiment, a conjugate of the invention contains a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a selective estrogen receptor modulator; an antibody such as trastuzumab; a steroid such as methotrexate; an antibiotic such as adriamycin; and a chemotherapeutic such as isofamide.

A taxane compound useful as a cancer chemotherapeutic agent in a conjugate of the invention can be, for example, docetaxel (Taxotere; Aventis Pharmaceuticals, Inc.; Parsippany, N.J.) or paclitaxel (Taxol; Bristol-Myers Squibb; Princeton, N.J.). See, for example, Chan et al., *J. Clin. Oncol.* 17:2341-2354 (1999), and Paridaens et al., *J. Clin. Oncol.* 18:724 (2000).

A cancer chemotherapeutic agent useful in a conjugate of the invention also can be an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J.P. Lippincott 1997); Harris et al., In "Cancer: Principles and practice of oncology," supra, 1997). In addition, doxorubicin has anti-angiogenic activity (Folkman, supra, 1997; Steiner, In "Angiogenesis: Key principles-Science, technology and medicine," pp. 449-454 (eds. Steiner et al.; Birkhauser Verlag, 1992)), which can contribute to its effectiveness in treating cancer.

An alkylating agent such as melphalan or chlorambucil also can be a cancer chemotherapeutic agent useful in a conjugate of the invention. Similarly, a vinca alkaloid such as vindesine, vinblastine or vinorelbine; or an antimetabolite such as 5-fluorouracil, 5-fluorouridine or a derivative thereof can be a cancer chemotherapeutic agent useful in a conjugate of the invention.

Another cancer chemotherapeutic agent useful in conjugates of the invention is a platinum agent. Such a platinum agent can be, for example, cisplatin or carboplatin as described, for example, in Crown, *Seminars in Oncol.* 28:28-37 (2001). Other cancer chemotherapeutic agents useful in a conjugate of the invention include, without limitation, methotrexate, mitomycin-C, adriamycin, ifosfamide and ansamycins.

A cancer chemotherapeutic agent for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a conjugate of the invention for treatment of breast cancer (Fisher et al., *J. Natl. Cancer Instit.* 90:1371-1388 (1998)).

A therapeutic agent useful in a conjugate of the invention can be an antibody such as a humanized monoclonal antibody. For example, the anti-epidermal growth factor receptor 2 (HER2) antibody, trastuzumab (Herceptin; Genentech, South San Francisco, Calif.) is a therapeutic agent useful in a conjugate of the invention for treating HER2/neu overexpressing breast cancers (Burris et al., supra, 2001; White et al., *Annu. Rev. Med.* 52:125-141 (2001)).

In another embodiment, a moiety useful in a conjugate of the invention is a cytotoxic agent. As used herein, the term "cytotoxic agent" refers to any molecule that results in cell death by any mechanism. Exemplary cytotoxic agents useful in a conjugate of the invention are doxorubicin, docetaxel and trastuzumab and antimicrobial peptides, described herein below.

A moiety useful in a conjugate of the invention also can be an anti-angiogenic agent. As used herein, an "anti-angiogenic agent" is a molecule that reduces or prevents angiogenesis, the growth and development of blood vessels. Vascular endothelial growth factor (VEGF) has been shown to be important for angiogenesis in many types of cancer, including breast cancer angiogenesis in vivo (Borgstrom et al., *Anticancer Res.* 19:4213-4214 (1999)). An anti-angiogenic agent can be, for example, an inhibitor or neutralizing antibody that inhibits a growth factor or other factor important for angiogenesis. In one embodiment, the anti-angiogenic agent is an anti-VEGF neutralizing monoclonal antibody (Borgstrom et al., supra, 1999). In another embodiment, the anti-angiogenic agent is a steroid or teratogen. In a further embodiment, the anti-angiogenic agent is a protein, peptide, or peptide fragment, such as endostatin, anastellin, thrombospondin, angiostatin, or a kringle peptide of angiostatin.

A moiety useful in a conjugate of the invention also can be a detectable label. As used herein, the term "detectable label" refers to any molecule which can be administered in vivo and subsequently detected. Exemplary detectable labels useful in the conjugates and methods of the invention include radiolabels and fluorescent molecules. Exemplary radionuclides include indium-111, technetium-99, carbon-11, and carbon-13. Fluorescent molecules include, without limitation, fluorescein, allophycocyanin, phycoerythrin, rhodamine, and Texas red.

The invention further provides a conjugate in which a homing molecule that selectively homes to tumor lymphatic vasculature is linked to an antimicrobial peptide, where the conjugate is selectively internalized by tumor lymphatic vasculature and exhibits a high toxicity to the tumor lymphatic vasculature, and where the antimicrobial peptide has low mammalian cell toxicity when not linked to the homing molecule. As used herein, the term "antimicrobial peptide" means a naturally occurring or synthetic peptide having antimicrobial activity, which is the ability to kill or slow the growth of one or more microbes and which has low mammalian cell toxicity when not linked to a homing molecule. An antimicrobial peptide, for example, can kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic α-helical structure (see U.S. Pat. No. 5,789,542; Javadpour et al., supra, 1996; Blondelle and Houghten, supra, 1992). An antimicrobial peptide also can be, for example, a β-strand/sheet-forming peptide as described in Mancheno et al., *J. Peptide Res.* 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, *Biopolymers* 37:105-122 (1995); Alvarez-Bravo et al., *Biochem. J.* 302:535-538 (1994); Bessalle et al., *FEBS* 274: 151-155 (1990); and Blondelle and Houghten in Bristol (Ed.), *Annual Reports in Medicinal Chemistry* pages 159-168 Academic Press, San Diego). As discussed further below, an antimicrobial peptide also can be an analog of a natural peptide, especially one that retains or enhances amphipathicity.

An antimicrobial peptide incorporated within a conjugate of the invention has low mammalian cell toxicity when not linked to a tumor homing molecule. Mammalian cell toxicity readily can be assessed using routine assays. For example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 μM for lytic activity, preferably concentrations greater than 200, 300, 500 or 1000 μM.

In one embodiment, the invention provides a conjugate in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art. $_D$(KLAKLAK)$_2$, for example, is an antimicrobial peptide which induces marked mitochondrial swelling at a concentration of 10 μM, significantly less than the concentration required to kill eukaryotic cells. An antimicrobial peptide that induces significant mitochondrial swelling at, for example, 50 μM, 40 μM, 30 μM, 20 μM, 10 μM, or less, is considered a peptide that promotes disruption of mitochondrial membranes.

An antimicrobial peptide portion can include, for example, the sequence (KLAKLAK)$_2$ (SEQ ID NO: 5), (KLAKKLA)$_2$ (SEQ ID NO: 6), (KAAKKAA)$_2$ (SEQ ID NO: 7), or (KLGKKLG)$_3$ (SEQ ID NO: 8), and, in one embodiment, includes the sequence $_D$(KLAKLAK)$_2$. A conjugate of the invention, which contains a homing molecule that selectively homes to tumor lymphatic vasculature linked to an antimicrobial peptide, can have, for example, the sequence CGNKRTRGC-GG-$_D$(KLAKLAK)$_2$ or GNKRTRG-GG-$_D$(KLAKLAK)$_2$.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, *Proteins: Structures and Molecular Properties* W.H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature; (Saberwal et al., *Biochim. Biophys. Acta* 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., *Biopolymers* 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic α-helical structure generally has an equivalent number of polar and nonpolar residues within the amphipathic domain and a sufficient number of basic residues to give the peptide an overall positive charge at neutral pH (Saberwal et al., *Biochim. Biophys. Acta* 1197: 109-131 (1994)). One skilled in the art understands that helix-promoting amino acids such as leucine and alanine can be advantageously included in an antimicrobial peptide of the invention (see, for example, Creighton, supra, 1984). Synthetic, antimicrobial peptides having an amphipathic α-helical structure are known in the art, for example, as described in U.S. Pat. No. 5,789,542 to McLaughlin and Becker.

It is understood by one skilled in the art of medicinal oncology that these and other agents are useful therapeutic agents, which can be used separately or together in the conjugates and methods of the invention. It further is understood that a conjugate of the invention can contain one or more of such therapeutic agents and that additional components can be included as part of the conjugate, if desired. For example, in some cases, it can be desirable to utilize an oligopeptide spacer between the homing molecule and the therapeutic agent (Fitzpatrick and Garnett, *Anticancer Drug Des.* 10:1-9 (1995)).

The invention also provides a method of imaging tumor lymphatic vasculature in a subject by administering to the subject a conjugate which contains a detectable label linked to a homing molecule that selectively homes to tumor lymphatic vasculature, and detecting the conjugate, thereby imaging the tumor lymphatic vasculature. In a method of the invention for imaging tumor lymphatic vasculature, the homing peptide can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide containing the amino acid sequence CGNKRTRGC (SEQ ID NO: 1), or a conservative variant or peptidomimetic thereof. A detectable label useful in an imaging method of the invention can be, for example, a radionuclide or a fluorescent molecule. Examples of radionuclides useful as detectable labels include, but are not limited to, indium-111, technetium-99, carbon-11, and carbon-13.

The methods of the invention for imaging tumor lymphatic vasculature can be useful for detecting the presence of tumor lymphatic vasculature associated with a variety of tumors. Following administration of a conjugate of the invention containing a detectable label, tumor lymphatic vasculature is visualized. If the image is positive for the presence of such tumor lymphatics, the tumor can be evaluated for size and quantity of lymphatic infiltration. These results provide valuable information to the clinician with regard to the stage of development of the cancer and the presence or probability of metastasis.

In a method of imaging tumor lymphatic vasculature, the conjugate administered contains a detectable label that allows detection or visualization of lymphatic vasculature in tumors, for example in breast tumors or in osteosarcomas. For in vivo diagnostic imaging of such tumor lymphatic vasculature, a homing molecule selective for the desired tumor is linked to a detectable label that, upon administration to the subject, is detectable external to the subject. Such a detectable label can be, for example, a gamma ray emitting radionuclide such as indium-113, indium-115 or technetium-99; following administration to a subject, the conjugate can be visualized using a solid scintillation detector.

The present invention also provides a method for reducing or inhibiting tumor metastasis in a subject. Metastasis occurs primarily through the lymphatic system, and the extent of lymph node involvement is a key prognostic factor for severity of disease. Lymphangiogenesis and the quantity of intratumoral lymphatic vessels in primary tumors have been correlated with tumor metastasis in animal experiments, for example, in breast cancer. (Skobe et al., *Nature Medicine* 7(2):192-198 (2001)). Intratumoral lymphatic vasculature can play an important role in the metastasis of many tumor types such as breast, colon, lung, thyroid, gastric, squamous cell cancers, mesotheliomas, osteosarcomas, and neuroblastomas.

According to the present invention, tumor metastasis is reduced or inhibited by administering to the subject a conjugate which contains a moiety linked to a homing molecule that selectively homes to tumor lymphatic vasculature, thereby reducing or inhibiting tumor metastasis. In such a method of the invention, the homing molecule can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide containing the amino acid sequence CGNKRTRGC (SEQ ID NO: 1), or a conservative variant or peptidomimetic thereof. A variety of moieties are useful in a method of the invention for reducing or inhibiting tumor metastasis. Such a moieties include, without limitation, cancer chemotherapeutic agents, cytotoxic agents and anti-lymphangiogenic agents.

The present invention further provides a method of reducing the number of tumor lymphatic vessels in a subject by administering to the subject a conjugate which contains a moiety linked to a homing molecule that selectively homes to tumor lymphatic vasculature, thereby reducing the number of tumor lymphatic vessels in the subject. In a method of the invention, the homing molecule can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide containing the amino acid sequence CGNKRTRGC (SEQ ID NO: 1), or a conservative variant or peptidomimetic thereof. A variety of moieties can be useful in a method of the invention for reducing the number of tumor lymphatic vessels including, without limitation, cancer chemotherapeutic agents, cytotoxic agents and anti-lymphangiogenic agents.

In addition, the present invention provides a method of treating cancer in a subject by administering to the subject a conjugate which contains a moiety linked to a homing molecule that selectively homes to tumor lymphatic vasculature. In a method of the invention, the homing molecule can be, for example, cyclic or otherwise conformationally constrained and further can be, for example, a peptide or peptidomimetic. In one embodiment, the homing molecule is a peptide containing the amino acid sequence GNKRTRG (SEQ ID NO: 2), or a conservative variant or peptidomimetic thereof. In another embodiment, the homing molecule is a peptide containing the amino acid sequence CGNKRTRGC (SEQ ID NO: 1), or a conservative variant or peptidomimetic thereof. A variety of moieties can be useful in a method of the invention for treating cancer in a subject including, but not limited to, cancer chemotherapeutic agents, cytotoxic agents and anti-lymphangiogenic agents.

As disclosed above, peptide SEQ ID NO: 1 selectively homes to tumor lymphatic vasculature and further has cytotoxic activity. Thus, the present invention further provides a method of treating cancer in a subject by administering to the subject a cytotoxic homing molecule that selectively homes to tumor lymphatic vasculature. In a method of the invention, the cytotoxic homing molecule can be, for example, cyclic or otherwise conformationally constrained and further can be, for example, a peptide or peptidomimetic. Furthermore, a cytotoxic homing molecule useful in a method of the invention can be, for example, a cytotoxic peptide that contains the amino acid sequence GNKRTRG (SEQ ID NO: 2), or a conservative variant or peptidomimetic thereof, or a cytotoxic peptide that contains the amino acid sequence CGNKRTRGC (SEQ ID NO: 1), or a conservative variant or peptidomimetic thereof.

The following examples are intended to illustrate but not limit the present invention.

EXAMPLE 1

Identification of Peptides that Bind to MDA-MB-435 Breast Carcinoma Cells In Vitro This example describes identification of a peptide that selectively homes to MDA-MB-435 breast carcinoma xenograft tumors using ex vivo and in vivo selections.

Several ex vivo selections were performed with 435 tumor cell suspensions prepared from MDA-MB-435 breast carcinoma xenografts grown in nude mice, as described below. Anti-mouse CD31 was used to deplete the tumor cell mixture of blood vessel endothelial cells prior to rescuing phage bound to the CD31-negative cell population. By the third ex vivo round, the phage pool bound a tumor cell suspension approximately 350-fold over control, nonrecombinant phage. The ex vivo preselected phage pool then was subjected to an in vivo selection round by injection into the tail vein of a nude mouse bearing an MDA-MB-435 tumor. Phage were then rescued from harvested xenograft tumor tissue.

Selected phage were enriched 30-fold relative to nonrecombinant T7 phage in the tumor. Forty-eight individual clones were randomly chosen from the in vivo selected pool, and the inserts sequenced as described below. Individual clones were assayed for the ability to bind cultured 435 cells as well as cell suspensions prepared from 435 tumors.

As shown in FIG. 1A, phage displaying the peptide CGNKRTRGC (SEQ ID NO: 1) bound to primary 435 tumor cell suspensions about 5000 times better than nonrecombinant phage. In contrast, phage displaying the spontaneous permutation CGEKRTRGC (SEQ ID NO: 3) or CGNKRTRGV (SEQ ID NO: 4) did not bind 435 tumor cell suspensions (see FIG. 1A). Addition of synthetic CGNKRTRGC (SEQ ID NO: 1) peptide inhibited binding of phage displaying the same peptide sequence.

Binding of the CGNKRTRGC (SEQ ID NO: 1)-displaying phage to the 435 tumor cell suspension correlated with copy number of the displayed peptide. As shown in FIG. 1B, there was a progressive decrease in phage binding when the peptide was displayed at 415 copies, 10 copies, or 1 copy. Thus, binding of SEQ ID NO: 1-displaying phage to a 435 tumor cell suspension was specific. The CGNKRTRGC (SEQ ID NO: 1)-displaying phage also bound to the 435 cells cultured for one to three days, although binding was weaker than to cells isolated from tumors. On average, binding to cultured 435 cells was about 50-fold greater than the binding observed with control, nonrecombinant phage.

These results demonstrate specific binding of phage displaying peptide SEQ ID NO: 1 to tumor cell suspensions prepared from breast carcinoma MDA-MB-435 xenografts.

A peptide display phage library with the general structure $CX_7C$, where C is cysteine and X is any amino acid, was constructed in T7 phage essentially as follows. Briefly, complementary oligonucleotides that encoded the random peptide insert as NNK codons, and had 5' Eco RI and 3' Hind III overhangs, were annealed. The resulting double stranded DNA was phosphorylated with T4 polynucleotide kinase (Novagen; Madison, Wis.) and ligated into 1 μg of T7Select415-1b vector arms. The ligated product was directly added to 50 μl of packaging extract and incubated for two hours, yielding $10^8$ pfu total recombinants. Following amplification of recombinants in 500 ml of liquid culture, purification of phage particles and sequencing of single stranded phage DNA was performed by standard methods.

Xenografts, tumor cell suspensions and ex vivo selections were performed essentially as follows. Nude Balb/c mice were subcutaneously injected with $1 \times 10^6$ MDA-MB-435 tumor cells to generate breast carcinoma xenografts. Human MDA-MB-435 breast carcinoma xenograft tumors were harvested 9 to 12 weeks after implantation, and tumor cell suspensions prepared using collagenase (0.5 mg/ml, Sigma).

435 tumor cell suspensions were incubated with the T7 phage-displayed $CX_7C$ library ($3.7 \times 10^{10}$ pfu) overnight at 4° C. The suspension was subjected to serial washes with 1% BSA in DME to remove unbound phage. Blood vessel endothelial cells were depleted from the tumor cell mixture using magnetic beads (Dynal; Lake Success, New York) coated with anti-mouse CD31 antibody (MEC 13.3; Pharminogen; San Diego, Calif.) according to the manufacturer's instructions. Phage bound to the CD31-negative cell population were rescued by adding bacteria, and the rescued phage titered and amplified in liquid culture.

EXAMPLE 2

Selective In Vivo Homing of Peptide CGNKRTRGC (SEQ ID NO: 1)

This example demonstrates that CGNKRTRGC (SEQ ID NO: 1)-displaying phage selectively home to MDA-MB-435 and KRIB human osteosarcoma tumors in vivo.

In vivo homing selectivity was analyzed essentially as follows. CGNKRTRGC (SEQ ID NO: 1)-displaying phage were injected into the tail vein of nude mice bearing either an MDA-MB-435 tumor, a KRIB osteosarcoma, a C8161 melanoma or an HL-60 leukemia cell xenograft. Phage subsequently were rescued from the respective tumors, as well as from several normal tissues (brain, kidney, liver, spleen, skin and breast).

As shown in FIG. 1C, CGNRTRKGC (SEQ ID NO: 1)-displaying phage homed to 435 and KRIB tumors in vivo. Although the strength of homing varied, the mean phage titer in tumor tissue was about 60-fold greater than for nonrecombinant phage in 435 tumors and 15-fold greater than for nonrecombinant phage in KRIB osteosarcomas. In contrast, the CGNKRTRGC (SEQ ID NO: 1)-displaying phage did not home in vivo to C8161 melanoma xenografts or HL-60 human leukemia xenografts. Furthermore, the CGNKRTRGC (SEQ ID NO: 1)-displaying phage did not home to normal brain, spleen, skin, kidney, or lung tissue. The CGNKRTRGC (SEQ ID NO: 1)-displaying phage appeared to home weakly to normal breast tissue (see FIG. 1D).

Homing of a CGEKRTRGC (SEQ ID NO: 3)-displaying phage, in which asparagine-3 is substituted with glutamate, to 435 tumors in vivo was only about 8% of that of the CGNKRTRGC (SEQ ID NO: 1) phage (see FIG. 1C). These in vivo homing results, which reproduced the binding results exhibited in tumor-derived cell suspensions, indicate that an asparagine or related residue at position three can contribute to homing activity.

In sum, these results demonstrate that peptide SEQ ID NO: 1 has selective homing activity and homes to breast cancer and osteosarcoma tumors in preference to normal tissues.

EXAMPLE 3

Internalization of the CGNKRTRGC (SEQ ID NO: 1)-Displaying Phage by Cells

This example demonstrates that CGNKRTRGC (SEQ ID NO: 1)-displaying phage are internalized by cells.

Increasing the time from the intravenous injection of the CGNKRTRGC (SEQ ID NO: 1)-displaying phage to rescue from the 435 tumors decreased phage recovery. To determine whether or not this decrease was due to internalization of phage by the cells, phage were rescued by lysing 435 tumor cells with a 0.5% solution of the detergent NP-40. As shown in FIG. 1E, 10 to 20 times more SEQ ID NO: 1-displaying phage were recovered with detergent than without detergent, indicating that phage were internalized by the tumor cells.

Figure 2B:
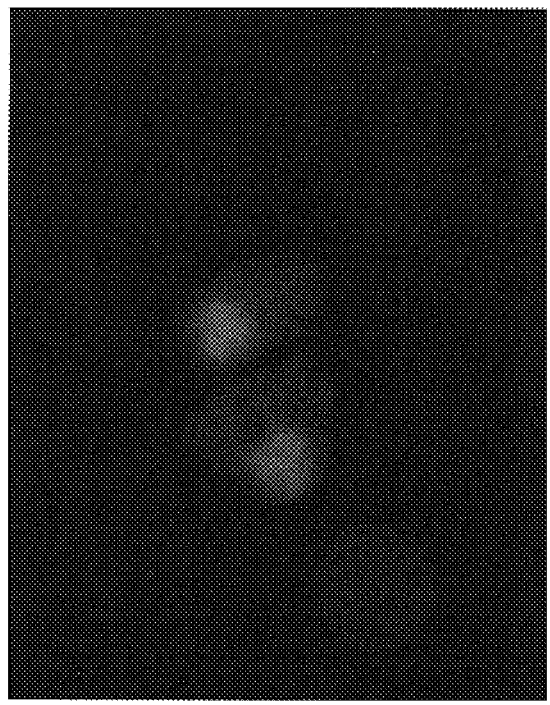

A fluorescein-conjugated CGNKRTRGC (SEQ ID NO: 1) peptide was utilized to further analyze cellular internalization and subcellular localization. Fluorescein-conjugated CGNKRTRGC (SEQ ID NO: 1) peptide and a fluorescein-conjugated control peptide containing three basic residues were synthesized according to Wender et al., *Proc. Natl. Acad. Sci.* 97:13003 (2000). The fluorescein-conjugated peptides were incubated with cultured MDA-MB-435 tumor cells for one to five hours at 37° C. As shown in FIG. 2A, fluorescein-labeled peptide CGNKRTRGC (SEQ ID NO: 1) was taken up by the 435 cells and translocated into the cell nucleus. In contrast, there was no detectable uptake by the cells of fluorescein-labeled control peptide (see FIG. 2B). Furthermore, fluorescein-conjugated CGNKRTRGC (SEQ ID NO: 1) peptide was internalized and transported into nuclei in vivo. Cultured 435 cells also internalized the CGNKRTRGC (SEQ ID NO: 1) phage, although the phage accumulated in the cytoplasm of the cells.

These results demonstrate that CGNKRTRGC (SEQ ID NO: 1)-displaying phage and a fluorescein-SEQ ID NO: 1 conjugate were internalized by cells.

EXAMPLE 4

Localization of CGNKRTRGC (SEQ ID NO: 1) Peptide with Lymphatic Markers VEGFR-3 and LYVE-1

This example demonstrates that peptide SEQ ID NO: 1 localizes to lymphatic vasculature.

A. Peptide SEQ ID NO: 1 Localizes to Vessels that are Negative for Blood Vessel Markers Localization of phage displaying SEQ ID NO: 1 was analyzed with anti-T7 phage antibody following intravenous injection of CGNKRTRGC (SEQ ID NO: 1)-displaying phage into the tail vein of nude mice carrying an MDA-MB-435 tumor. CGNKRTRGC (SEQ ID NO: 1)-displaying phage localized in vessel-like structures and in some single cells within the 435 tumors. The vessels in which the phage localized were negative for Meca-32, a marker specific for blood vessels, and also negative for CD31, which is expressed more prominently in blood vessels than in lymphatic vessels. Similar results were obtained by a phage overlay assay in which phage were added onto frozen tissue sections, rather than being injected into the mice.

Figure 3A:
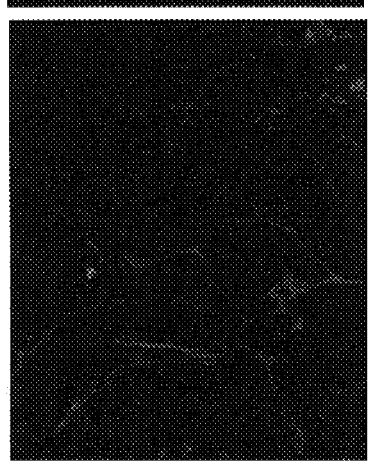
FIG. 3 shows localization of fluorescent peptide CGNKRTRGC (SEQ ID NO: 1) in tumors following intravenous injection. (A-C) Fluorescent peptide CGNKRTRGC (SEQ ID NO: 1) staining (green). (D-F) Tomato lectin staining detected with streptavidin-conjugated Alexa 594 (red). (G-I) Peptide and blood vessel staining present in the same microscopic field.
Figure 3B:
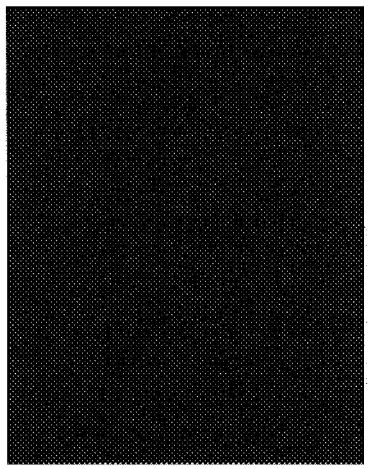
Figure 3C:
Figure 3D:
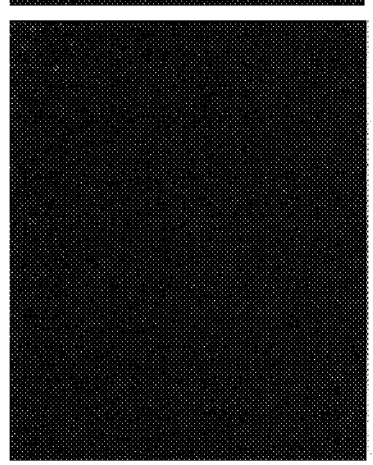
Figure 3E:
Figure 3F:
Figures 3G, 3H, 3I:
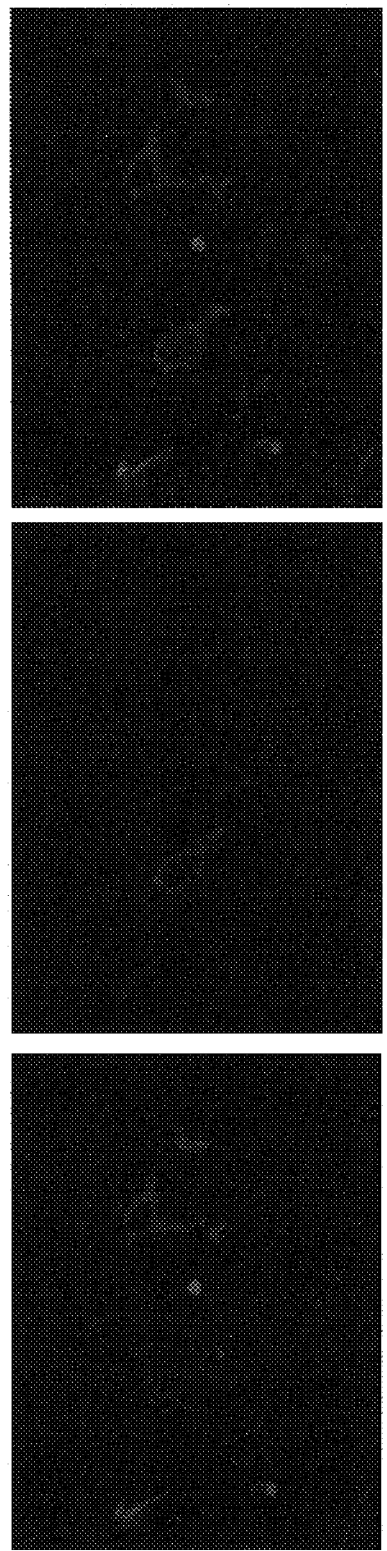

When fluorescein-conjugated CGNKRTRGC (SEQ ID NO: 1) peptide was injected into the tail vein of 435 tumor-bearing mice, the fluorescein-conjugated peptide localized in vessel-like structures and in individual cells within the tumor. These vessels were negative for the CD31 and Meca-32 blood vessel markers. As seen in FIGS. 3A-C, there was a notable lack of co-localization of fluorescein-conjugated peptide with blood vessels labeled with biotin-conjugated tomato lectin. Even where portions of the tumor contained both peptide and blood vessels, their locations were distinct (FIGS. 3G-I). These data indicate that the vessel-like structures targeted by the CGNKRTRGC (SEQ ID NO: 1) peptide were not blood vessels.

Several normal tissues also were studied for localization of the CGNKRTRGC (SEQ ID NO: 1) peptide. Fluorescence was seen only in the kidney tubuli, which may be a result of uptake of peptide from the glomerular filtrate. The fluorescein-labeled control peptide was also detected to the same extent in the kidney tubuli after intravenous injection, but was not detected in tumor tissue, indicating that peptide localization to kidney tubuli was non-specific.

An anti-T7 antiserum was prepared by immunizing New Zealand white rabbits with $10^{10}$ pfu of T7 nonrecombinant phage (Novagen). The initial immunization performed in complete Freund's Adjuvant, while boosters were administered in incomplete Freund's Adjuvant. The antibody titer was estimated by ELISA, and the antiserum was absorbed against BLT5615 bacterial and mouse liver lysates. Phage were detected using anti-T7 phage antiserum (1:1000 dilution) and goat anti-rabbit secondary antibody conjugated to fluorescein.

Detection of fluorescent peptides and biotin-conjugated tomato lectin was performed as follows. Fluorescein-conjugated peptide CGNKRTRGC (SEQ ID NO: 1) was prepared as described above. The peptide (100 µg in 200 µl of PBS) was injected into the tail vein of mice bearing MDA-MB-435 breast carcinoma tumors. After 10 minutes, biotin-conjugated *lycopersicon esculentum* (tomato) lectin (100 µg in 200 µl of PBS; Vector; Burlingame, Calif.) was also injected into the tail vein. After 5 minutes, the mouse was perfused through the heart with 4% paraformaldehyde. Tissues were removed and frozen in O.C.T. embedding medium (Tissue-Tek; Torrence, Calif.). Blood vessels were visualized by detecting the tomato lectin with streptavidin-conjugated Alexa 594 (Molecular Probes; Eugene, Oreg.). Green staining indicated the presence of peptide SEQ ID NO: 1, while red staining indicated the presence of tomato lectin.

B. Peptide CGNKRTRGC (SEQ ID NO: 1) Homes to Lymphatic Vessels and Cells within Tumors MDA-MB-435 breast carcinoma tumors contain lymphatic vessels that are positive for markers of lymphatic endothelial cells. To determine whether CGNKRTRGC (SEQ ID NO: 1) homed to the 435 tumor lymphatics, tumor sections were stained with the lymphatic markers VEGFR-3 and LYVE-1. Lymphatic vessels were visualized using a rat anti-mouse VEGFR-3 antibody or with rabbit anti-LYVE-1 antibody produced as described below.

Figure 4A:
FIG. 4 shows distinct localization of lymphatic vessel markers and blood vessel markers. Lymphatic vessels were visualized in 435 tumor sections using rabbit anti-LYVE1 and goat anti-rabbit Alexa 594 and appear red in the photomicrographs. Blood vessels were labeled with fluorescein-conjugated tomato lectin and appear green in photomicrographs.
Figure 4B:
Figure 4C:
Figure 5A:
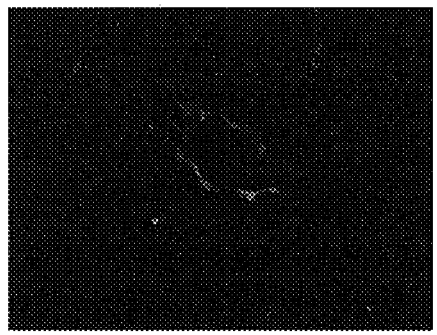
FIG. 5 shows co-localization of fluorescein-conjugated peptide CGNKRTRGC (SEQ ID NO: 1) with the lymphatic markers VEGFR-3 and LYVE-1. (A,C,E) Fluorescein-conjugated CGNKRTRGC (SEQ ID NO: 1; green) and lymphatic marker VEGFR-3 (red). (G) Fluorescein-conjugated CGNKRTRGC (SEQ ID NO: 1; green) and lymphatic marker LYVE-1 (red). (B, D, F, H) Fluorescein-conjugated SEQ ID NO: 1 (green) and DAPI nuclear staining (blue).
Figure 5B:
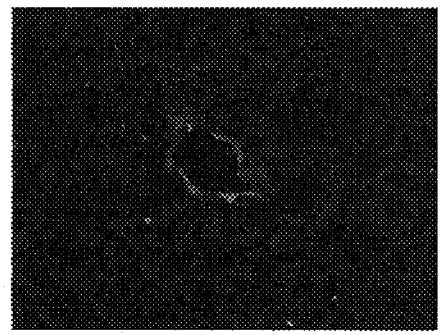
Figure 5C:
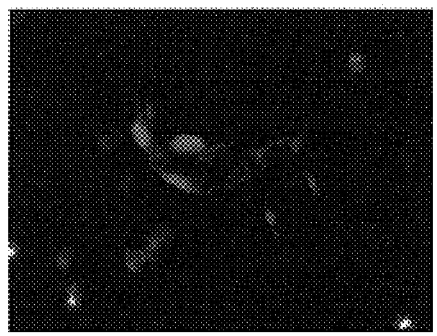
Figure 5D:
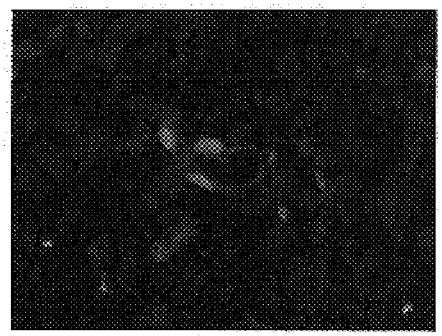
Figure 5E:
Figure 5F:
Figure 5G:
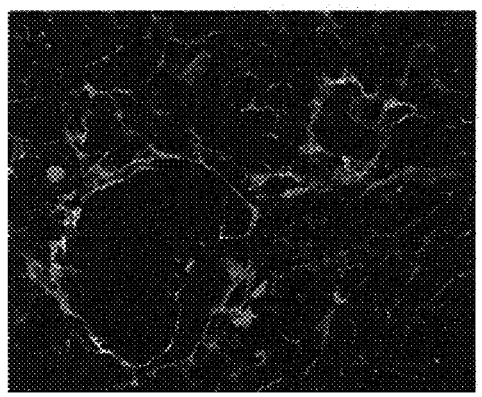
Figure 5H:
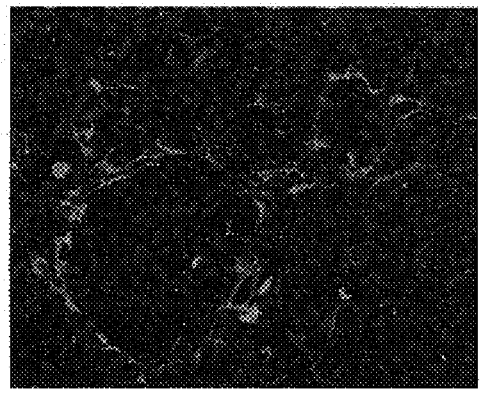

As shown in FIG. 4, the vessel-like structures in the tumor stained with antibodies against both lymphatic markers. Only a small number of these vessels were blood vessels, as shown by the rare occurrence of overlap of VEGFR-3 and labeling of injected tomato lectin. In contrast, intravenously injected fluorescein-conjugated CGNKRTRGC peptide SEQ ID NO: 1 co-localized with VEGFR-3 and LYVE-1 staining in 435 tumor tissue (see FIG. 5). Furthermore, the fluorescein-conjugated peptide (SEQ ID NO: 1) accumulated in the nuclei lining the vessel-like structures (FIG. 5C). These results indicate that peptide SEQ ID NO: 1 selectively homes to tumor lymphatic vasculature.

The CGNKRTRGC (SEQ ID NO: 1) peptide also accumulated in VEGFR-3 positive single cells within the tumor and in structures that resembled the staining pattern observed in collapsed lymphatic vessels in human tissues (Fukuda et al., *The Prostate* 44:332 (2000) and Ebata et al., *Microvasc. Res.* 61: 40 (2001)); these structures were only occasionally positive for VEGFR-3 or LYVE-1. The VEGFR-3 positive single cells were not macrophages, which can infiltrate tumors, as evidenced by a lack of co-localization of SEQ ID NO: 1 and the macrophage marker F4/80. The VEGFR-3 positive single cells can be involved in the development of lymphatic endothelial cells, for example, lymphangioblasts (Schneider et al., *Dev. Dyn.* 216: 311 (1999) or migrating endothelial cells of a mixed type such as those described by Wigle et al., *Cell* 98: 769 (1999).

LYVE-1 antibody was produced by immunizing New Zealand White rabbits with a peptide encoding the 19 most C-terminal residues of mouse LYVE-1 (Prevo et al., *J. Biol. Chem.* 276:19420 (2001)) conjugated to keyhole limpet hemocyanin (KLH; Pierce; Iselin, N.J.). The initial immunization was done in complete Freund's Adjuvant, with boosters performed in incomplete Freund's Adjuvant. Specific antibody was obtained following affinity purification with the peptide coupled to Sulfolink Gel (Pierce). Tissues were processed for fifteen minutes following injection with fluorescein-conjugated peptide using rat anti-mouse anti-VEGFR-3, and rabbit anti-LYVE-1. The anti-LYVE-1 antibody was used at a 1:500 dilution on cryo sections, followed by detection with goat anti-rabbit secondary antibody conjugated to Alexa 594 (Molecular Probes).

EXAMPLE 5

In Vivo Homing of Phage Displaying Peptide CGNKRTRGC (SEQ ID NO: 1) Following Subcutaneous Injection This example demonstrates in vivo homing of phage displaying SEQ ID NO: 1 to MDA-MB-435 tumor lymphatics following subcutaneous injection.

Subcutaneous and intravenous injection of phage was performed as follows. CGNKRTRGC (SEQ ID NO: 1) phage ($5 \times 10^9$ PFU) were subcutaneously (s.c.) injected about 3 cm from a 435 tumor or into the tail vein (i.v.) of a 435 tumor-bearing mouse. After 12 minutes, the mouse was perfused through the heart with 20 ml of PBS, and the tumor and control organ were removed. Unbound phage were removed by several washes, and the bound phage were recovered by adding bacteria and titrated.

Figure 6:
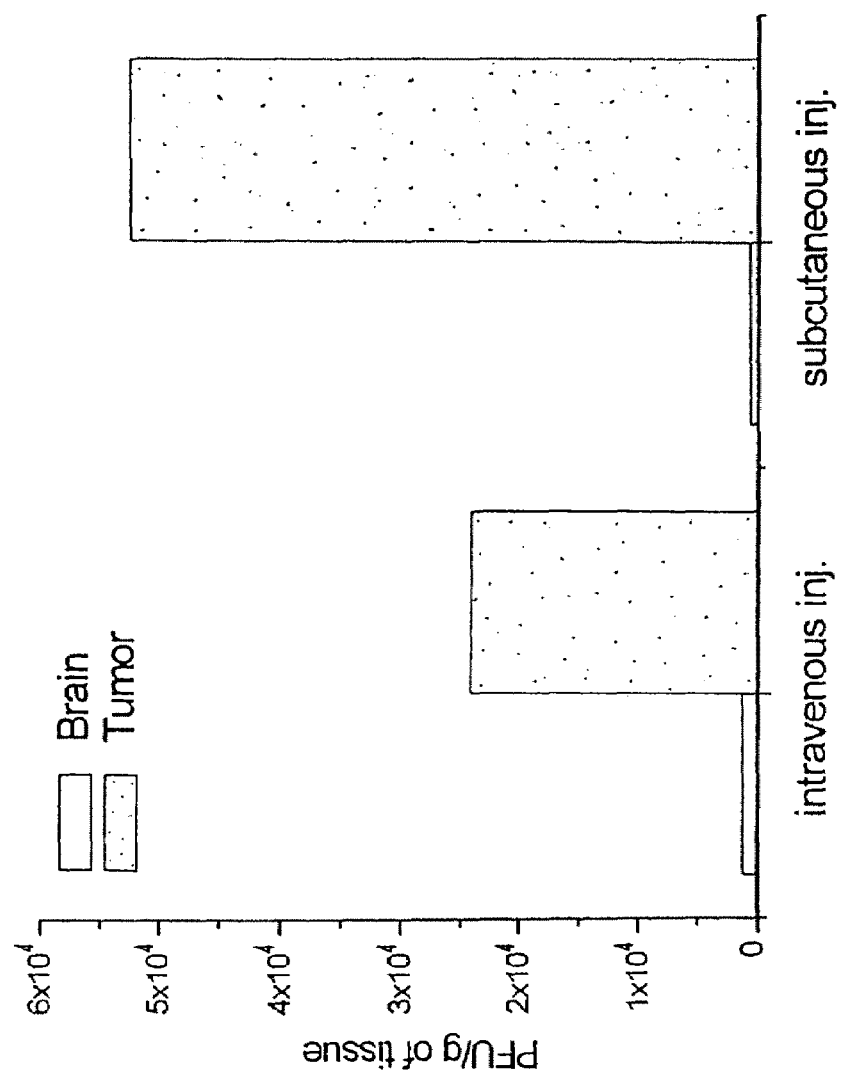
FIG. 6 shows homing of CGNKRTRGC (SEQ ID NO: 1) phage to MDA-MB-435 xenograft tumors or brain following intravenous or subcutaneous injection.

As shown in FIG. 6, a striking enrichment of SEQ ID NO: 1-bearing phage was observed in the tumor relative to nonrecombinant phage after subcutaneous injection. As further shown in FIG. 6, a significantly lower background of CGNKRTRGC (SEQ ID NO: 1) phage was present in the control organ following subcutaneous injection as compared to the background resulting from intravenous injection. These results further demonstrate the lymphatic vessel specificity of the CGNKRTRGC (SEQ ID NO: 1) peptide and indicate that SEQ ID NO:1-displaying phage and peptide can accumulate in the lymphatic vessels of a tumor within minutes after having been injected intravenously.

EXAMPLE 6

Cytotoxic Activity of Peptide CGNKRTRGC (SEQ ID NO: 1)

This example demonstrates that peptide SEQ ID NO: 1 has cytotoxic activity in cell culture and in vivo.

Cultured MDA-MB-435 cells were incubated with a control peptide (CGEKRTRGC; SEQ ID NO: 3) or with CGNKRTRGC (SEQ ID NO: 1) at 37° C. for 1, 2 or 4 hours. After staining with trypan blue, which is taken up by cells that are dead or dying, the total number of cells were counted, and the percentage of trypan blue stained cells determined. As shown in FIG. 7, a significantly enhanced cytotoxic effect was observed with peptide SEQ ID NO: 1 as compared to control peptide SEQ ID NO: 3 at the later time points. In particular, after four hours incubation, at least 7-fold greater trypan blue uptake was evident in cell cultures incubated with peptide SEQ ID NO: 1 as compared to cultures incubated with control peptide. These results indicate that peptide SEQ ID NO: 1 has cytotoxic activity.

A tumor treatment study was performed using MDA-MB-435 human breast carcinoma cell xenografts prepared by subcutaneously injecting $1 \times 10^6$ cells in 200 µl PBS into nude mice. Mice (five per group) were treated intravenously twice a week with 67 nmol CGNKRTRGC peptide (SEQ ID NO: 1) or with PBS starting four weeks after tumor implantation. Tumor volumes were measured once a week for four weeks. As shown in FIG. 8, the mean tumor volume was at least several fold less in mice administered peptide SEQ ID NO: 1 than in mice administered PBS alone beginning after about two weeks of treatment. These results demonstrate that peptide CGNKRTRGC (SEQ ID NO: 1) has cytotoxic activity in vivo and indicate that this peptide and peptides that bind the same receptor can be useful for slowing or preventing tumor growth in vivo.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A conjugate, comprising a moiety linked to a homing molecule that selectively homes to tumor lymphatic vasculature, wherein said homing molecule is a peptide comprising the amino acid sequence GNKRTRG (SEQ ID NO: 2).

2. The conjugate of claim 1, wherein said peptide is not an antibody or antigen-binding fragment thereof.

3. The conjugate of claim 1, wherein the peptide portion of said conjugate has a length of at most 200 residues.

4. The conjugate of claim 3, wherein the peptide portion of said conjugate has a length of at most 50 residues.

5. The conjugate of claim 1, wherein said peptide is conformationally constrained.

6. The conjugate of claim 1, wherein said peptide is cyclic.

7. The conjugate of claim 1, wherein said homing molecule is a peptide comprising the amino acid sequence CGNKRTRGC (SEQ ID NO: 1).

8. The conjugate of claim 7, wherein said homing molecule is conformationally constrained.

9. The conjugate of claim 7, wherein said homing molecule is cyclic.

10. The conjugate of claim 1, wherein said moiety is a therapeutic agent.

11. The conjugate of claim 1, wherein said moiety is a cancer chemotherapeutic agent.

12. The conjugate of claim 1, wherein said moiety is a cytotoxic agent.

13. The conjugate of claim 1, wherein said moiety is an anti-lymphangiogenic agent.

14. The conjugate of claim 1, wherein said moiety is a detectable label.

15. The conjugate of claim 1, wherein said moiety is a phage.

16. The conjugate of claim 1, comprising at least two homing molecules that each selectively homes to tumor lymphatic vasculature.

17. The conjugate of claim 16, comprising at least ten homing molecules that each selectively homes to tumor lymphatic vasculature.

18. The conjugate of claim 17, comprising at least 100 homing molecules that each selectively homes to tumor lymphatic vasculature.

19. The conjugate of claim 18, wherein said moiety is a phage.

20. The conjugate of claim 1, comprising at least two homing molecules that each selectively homes to tumor lymphatic vasculature, said homing molecules each independently comprising the amino acid sequence GNKRTRG (SEQ ID NO: 2).

21. The conjugate of claim 20, comprising at least ten homing molecules that each selectively homes to tumor lymphatic vasculature, said homing molecules each independently comprising a peptide comprising the amino acid sequence GNKRTRG (SEQ ID NO: 2).

22. The conjugate of claim 21, comprising at least 100 homing molecules that each selectively homes to tumor lymphatic vasculature, said homing molecules each independently comprising a peptide comprising the amino acid sequence GNKRTRG (SEQ ID NO: 2).

23. The conjugate of claim 22, wherein said moiety is a phage.

24. The conjugate of claim 1, wherein the peptide portion of said conjugate has a length of less than 20 residues.

25. The conjugate of claim 1, wherein the peptide portion of said conjugate has a length of less than 15 residues.

26. The conjugate of claim 1, wherein the peptide portion of said conjugate has a length of less than 12 residues.

27. The conjugate of claim 1, wherein the peptide portion of said conjugate has a length of less than 10 residues.

28. The conjugate of claim 1, wherein the peptide portion of said conjugate has a length of less than 9 residues.

29. The conjugate of claim 1, wherein the peptide portion of said conjugate has a length of less than 8 residues.

30. The conjugate of claim 1, wherein the peptide portion of said conjugate consists of the amino acid sequence GNKRTRG (SEQ ID NO: 2).

31. The conjugate of claim 7, wherein the peptide portion of said conjugate has a length up to 200 residues.

32. The conjugate of claim 7, wherein the peptide portion of said conjugate has a length up to 50 residues.

33. The conjugate of claim 7, wherein the peptide portion of said conjugate has a length of less than 20 residues.

34. The conjugate of claim 7, wherein the peptide portion of said conjugate has a length of less than 15 residues.

35. The conjugate of claim 7, wherein the peptide portion of said conjugate has a length of less than 12 residues.

36. The conjugate of claim 7, wherein the peptide portion of said conjugate has a length of less than 10 residues.

37. The conjugate of claim 21, wherein the peptide portion of said conjugate consists of the amino acid sequence CGNKRTRGC (SEQ ID NO: 1).

* * * * *

```
                       SEQUENCE LISTING

<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: Synthetic construct

<400> SEQUENCE: 1

Cys Gly Asn Lys Arg Thr Arg Gly Cys
 1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic construct

<400> SEQUENCE: 2

Gly Asn Lys Arg Thr Arg Gly
 1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Cys Gly Glu Lys Arg Thr Arg Gly Cys
 1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic construct

<400> SEQUENCE: 4

Cys Gly Asn Lys Arg Thr Arg Gly Val
 1               5

<210> SEQ ID NO 5
<211> LENGTH: 14
<212> TYPE: PRT
```

-continued

```
<213> ORGANISM: Artificial Sequence
<220> FEATURE:
<223> OTHER INFORMATION: Synthetic construct

<400> SEQUENCE: 5

Lys Leu Ala Lys Leu Ala Lys Lys Leu Ala Lys Leu Ala Lys
  1               5                  10

<210> SEQ ID NO 6
<211> LENGTH: 14
<212> TYPE: PRT
<213> ORGANISM: Artificial Sequence
<220> FEATURE:
<223> OTHER INFORMATION: Synthetic construct

<400> SEQUENCE: 6

Lys Leu Ala Lys Lys Leu Ala Lys Leu Ala Lys Lys Leu Ala
  1               5                  10

<210> SEQ ID NO 7
<211> LENGTH: 14
<212> TYPE: PRT
<213> ORGANISM: Artificial Sequence
<220> FEATURE:
<223> OTHER INFORMATION: Synthetic construct

<400> SEQUENCE: 7

Lys Ala Ala Lys Lys Ala Ala Lys Ala Ala Lys Lys Ala Ala
  1               5                  10

<210> SEQ ID NO 8
<211> LENGTH: 21
<212> TYPE: PRT
<213> ORGANISM: Artificial Sequence
<220> FEATURE:
<223> OTHER INFORMATION: Synthetic construct

<400> SEQUENCE: 8

Lys Leu Gly Lys Lys Leu Gly Lys Leu Gly Lys Lys Leu Gly Lys Leu
  1               5                  10                  15

Gly Lys Lys Leu Gly
                20
```